(12) United States Patent
Buchalter

(10) Patent No.: US 12,036,309 B2
(45) Date of Patent: Jul. 16, 2024

(54) CERTIFIED NATURAL SKIN CARE PRODUCTS

(71) Applicant: Product on the Go, LLC, Delray Beach, FL (US)

(72) Inventor: Sharon Buchalter, Delray Beach, FL (US)

(73) Assignee: Product on the Go, LLC, Delray Beach, FL (US)

( * ) Notice: Subject to any disclaimer, the term of this patent is extended or adjusted under 35 U.S.C. 154(b) by 504 days.

(21) Appl. No.: 17/294,739

(22) PCT Filed: Nov. 21, 2019

(86) PCT No.: PCT/US2019/062693
§ 371 (c)(1),
(2) Date: May 18, 2021

(87) PCT Pub. No.: WO2020/107000
PCT Pub. Date: May 28, 2020

(65) Prior Publication Data
US 2022/0016018 A1      Jan. 20, 2022

Related U.S. Application Data

(60) Provisional application No. 62/772,004, filed on Nov. 27, 2018, provisional application No. 62/771,995, filed on Nov. 27, 2018, provisional application No. 62/772,002, filed on Nov. 27, 2018, provisional application No. 62/770,635, filed on Nov. 21, 2018, provisional application No. 62/770,630, filed on Nov. 21, 2018, provisional application No. 62/770,627, filed on Nov. 21, 2018, provisional application No. 62/770,638, filed on Nov. 21, 2018.

(51) Int. Cl.
| | | |
|---|---|---|
| *A61K 8/92* | (2006.01) |
| *A61K 8/27* | (2006.01) |
| *A61K 8/67* | (2006.01) |
| *A61K 8/9789* | (2017.01) |
| *A61K 8/9794* | (2017.01) |
| *A61K 8/98* | (2006.01) |
| *A61Q 19/00* | (2006.01) |

(52) U.S. Cl.
CPC ............. *A61K 8/922* (2013.01); *A61K 8/27* (2013.01); *A61K 8/678* (2013.01); *A61K 8/9789* (2017.08); *A61K 8/9794* (2017.08); *A61K 8/987* (2013.01); *A61Q 19/005* (2013.01)

(58) Field of Classification Search
None
See application file for complete search history.

(56) References Cited

U.S. PATENT DOCUMENTS

| | | |
|---|---|---|
| 8,911,801 B2 | 12/2014 | Debaun et al. |
| 2011/0229538 A1 | 9/2011 | Matravers et al. |
| 2015/0297485 A1 | 10/2015 | Kleinen et al. |

FOREIGN PATENT DOCUMENTS

| | | |
|---|---|---|
| CN | 105030585 B | 9/2017 |
| CN | 10874347 A | 11/2018 |

OTHER PUBLICATIONS

International Search Report and Written Opinion dated Feb. 3, 2020, issued in PCT Application No. PCT/US2019/062693, filed Nov. 21, 2019.
International Preliminary Report on Patentability received for PCT Patent Application No. PCT/US19/62693, dated Jun. 3, 2021, 9 pages.

*Primary Examiner* — Susan Hoffman
(74) *Attorney, Agent, or Firm* — Workman Nydegger

(57) ABSTRACT

Disclosed are certified natural skin compositions and related methods of use. Certified natural compositions include diaper rash compositions, antioxidant sunscreen compositions, with or without natural sparkle or shimmer ingredient(s), and after-sun, tan-enhancing bronzer, skin toner or moisturizer composition with natural sparkle or shimmer. The inventive natural skin compositions are specifically formulated with natural ingredients, such that the products are suitable for certification as "natural" and/or "organic" products, and more particularly formulated with a variety of high-quality ingredients that care for and protect skin.

3 Claims, 7 Drawing Sheets

CERTIFIED NATURAL SKIN CARE PRODUCTS

BACKGROUND

1. Technical Field

The present disclosure relates to skin products, particularly skin products made with natural ingredients. Specifically, the present disclosure relates to skin care products formulated with natural ingredients, such that the products are suitable for certification as "natural" and/or "organic" products.

2. Related Technology

The demand for "natural" skin products in the U.S. and around the world has led manufacturers and retailers to seek industry certifications. Consumers desire and even demand certified skin products that are made "cruelty free" (e.g., without animal products or animal testing) and/or with "natural," "organic," and/or "non-synthetic" ingredients.

However, product manufacturers and retailers are often conflicted because synthetic, non-natural products or ingredients may be better suited to accomplish a particular skin care need, such as moisturizing, softening or repairing damage to skin, preventing or treating skin infection, and preventing or protecting against overexposure to electromagnetic radiation or forms of oxidative stress, such as free radicals. Moreover, synthetic, non-natural products or ingredients may be better suited for longer shelf-life, as they may include artificial, synthetic, non-natural preservatives, solubilizing agents, surfactants, and so forth.

Some skin products, such as essential oils, lip balm, and various lotions, include only a small number of ingredients and, consequently, are relatively easy to manufacture using only certified natural ingredients. More complex formulations, however, include a variety of ingredients and are, therefore, much more difficult to manufacture using only certified natural ingredients. Complex skin formulations that contain a variety of ingredients may also be expensive to formulate and manufacture. Complex skin formulations with a variety of ingredients and that are suitable for certification as "natural" may be prohibitively expensive to manufacture or sell; both in the cost of the organic or natural ingredient, as well as the administrative cost associated with compliance, verification, and industry certification. For these reasons, many skin product formulators, manufacturers, and retailers forego coveted certification as "natural" or "organic" and, instead, include some natural and some artificial, synthetic ingredients, so that the product can be labeled as being made with "natural ingredients," while the formulators, manufacturers, and/or retailers avoid the expense associated with a certified "natural" or "organic" product.

Accordingly, there continues to be a need for natural skin products, specifically skin products formulated with natural ingredients, such that the products are suitable for certification as "natural" and/or "organic" products, and more particularly formulated with a variety of high quality ingredients that care for and protect skin.

BRIEF DESCRIPTION OF THE DRAWINGS

Various embodiments of the present disclosure will be discussed with reference to the appended drawings. It is appreciated that the drawings depict only typical embodiments of the presents disclosure and are not to be considered limiting of its scope.

BRIEF SUMMARY

Figure 1:
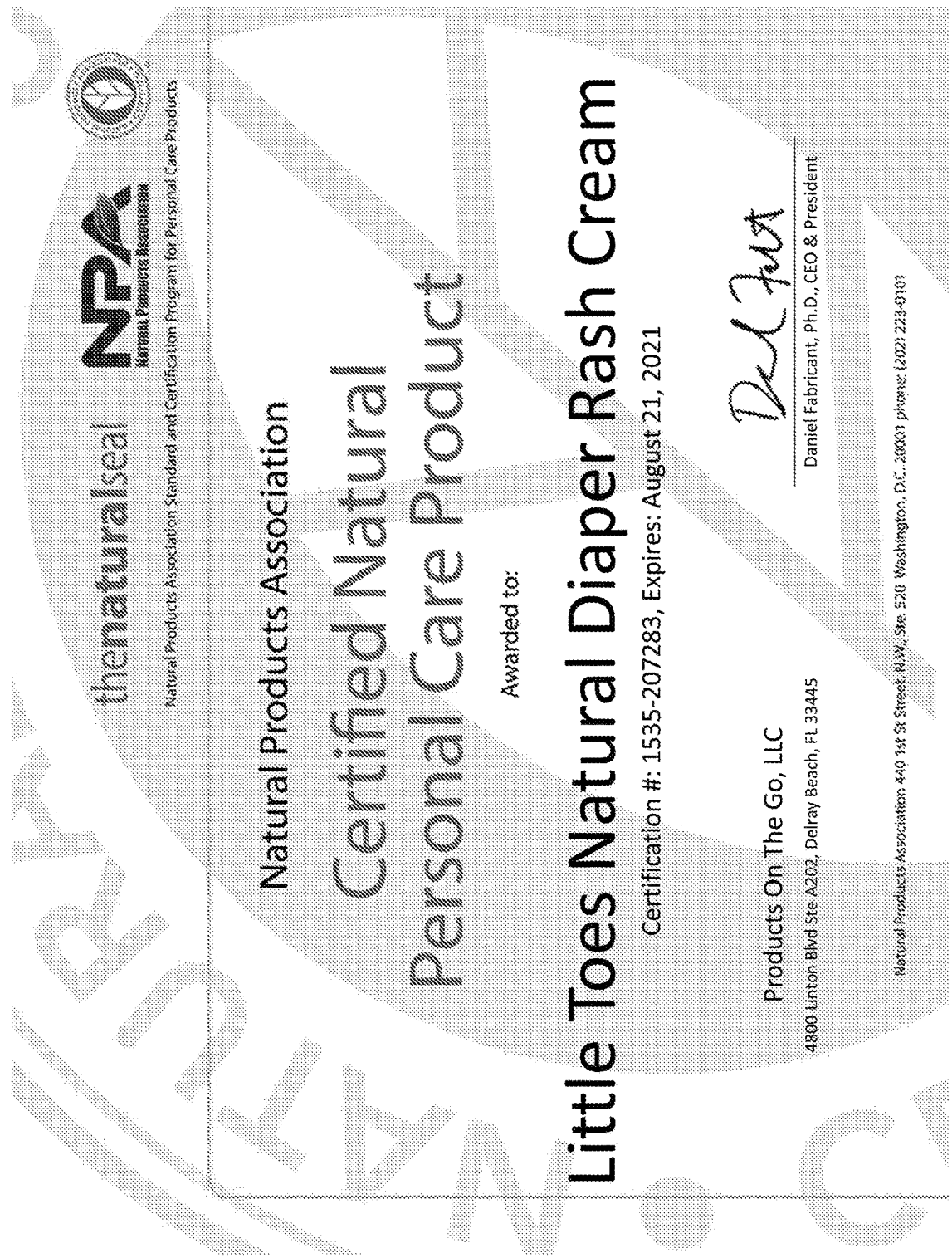
FIG. 1 is a copy of an actual, valid certification from the Natural Products Association of a Natural Diaper Rash Cream composition in accordance with one or more embodiments of the present disclosure.

Embodiments, implementations, and/or aspects of the present disclosure solve one or more of the foregoing or other problems in the art with certified natural diaper rash compositions, certified natural, fragrance-free diaper rash compositions, certified natural sunscreen compositions (with and without natural sparkle or shimmer), and certified natural after-sun bronzer, toner, and/or moisturizer compositions with natural sparkle or shimmer.

In a first aspect, a certified natural diaper rash composition, preferably for use in treating or preventing dermatitis or diaper rash, is disclosed.

The certified natural diaper rash composition can comprise zinc oxide, *Aloe vera* (juice) or extract thereof, beeswax, *Butyrospermum Parkii* (shea) butter, *Cocos nucifera* (coconut) oil, *Lavandula angustifolia* (lavender) oil, *Cucumis sativus* (cucumber) or extract thereof, *Glycyrrhiza glabra* (licorice) or extract thereof, *Calendula officinalis* (calendula) or extract thereof, Tocopherol, *Chamomilla recutita* (chamomile) oil, and *Helianthus annuus* (sunflower) seed oil.

The certified natural diaper rash composition can comprise 5-20%, w/w, zinc oxide; 10-30%, w/w, *Aloe vera* (juice) or extract thereof; 5-15%, w/w, beeswax; 5-15%, w/w, *Butyrospermum Parkii* (shea) butter; 1-5%, w/w, *Cocos nucifera* (coconut) oil; 0.01-1%, w/w, *Lavandula angustifolia* (lavender) oil; 0.01-1%, w/w, *Cucumis sativus* (cucumber) or extract thereof; 0.01-1%, w/w, *Glycyrrhiza glabra* (licorice) or extract thereof; 0.01-1%, w/w, *Calendula officinalis* (calendula) or extract thereof; 0.01-1%, w/w, tocopherol; 0.01-1%, w/w, *Chamomilla recutita* (chamomile) oil; and *Helianthus annuus* (sunflower) seed oil q.s. to 100%.

The certified natural diaper rash composition can comprise about 12%, w/w, zinc oxide; about 20%, w/w, *Aloe vera* (juice) or extract thereof; about 11.5%, w/w, beeswax; about 11%, w/w, *Butyrospermum Parkii* (shea) butter; about 3%, w/w, *Cocos nucifera* (coconut) oil; about 0.2%, w/w, *Lavandula angustifolia* (lavender) oil; about 0.1%, w/w, *Cucumis sativus* (cucumber) or extract thereof; about 0.1%, w/w, *Glycyrrhiza glabra* (licorice) or extract thereof; about 0.1%, w/w, *Calendula officinalis* (*calendula*) or extract thereof; about 0.1%, w/w, tocopherol; about 0.1%, w/w, *Chamomilla recutita* (chamomile) oil; and *Helianthus annuus* (sunflower) seed oil q.s. to 100%.

The certified natural diaper rash composition can (i) consist or consist essentially of certified natural and/or organic ingredients or (ii) be substantially free or devoid of synthetic ingredients that negate natural certification.

A method of treating or preventing dermatitis or diaper rash can comprise applying a certified natural diaper rash composition of the present disclosure to a selected skin area having dermatitis or diaper rash and, optionally, leaving the certified natural diaper rash composition in contact with the selected skin are for a first period of time (e.g., at least 1 hour, etc.).

In a second aspect, a certified natural, fragrance-free diaper rash composition, preferably for use in treating or preventing dermatitis or diaper rash, is disclosed.

The certified natural, fragrance-free diaper rash composition can comprise zinc oxide, *Aloe vera* (juice) or extract thereof, beeswax, *Butyrospermum Parkii* (shea) butter, *Cocos nucifera* (coconut) oil, *Cucumis sativus* (cucumber) or extract thereof, *Calendula officinalis* (*calendula*) or extract thereof, Tocopherol, and *Helianthus annuus* (sunflower) seed oil.

The certified natural, fragrance-free diaper rash composition can comprise 5-20%, w/w, zinc oxide; 10-30%, w/w, *Aloe vera* (juice) or extract thereof; 5-15%, w/w, beeswax; 5-15%, w/w, *Butyrospermum Parkii* (shea) butter; 1-5%, w/w, *Cocos nucifera* (coconut) oil; 0.01-1%, w/w, *Cucumis sativus* (cucumber) or extract thereof; 0.01-1%, w/w, *Calendula officinalis* (*calendula*) or extract thereof; 0.01-1%, w/w, tocopherol; and *Helianthus annuus* (sunflower) seed oil q.s. to 100%.

The certified natural, fragrance-free diaper rash composition can comprise about 12%, w/w, zinc oxide; about 20%, w/w, *Aloe vera* (juice) or extract thereof; about 11.5%, w/w, beeswax; about 11%, w/w, *Butyrospermum Parkii* (shea) butter; about 3%, w/w, *Cocos nucifera* (coconut) oil; about 0.1%, w/w, *Cucumis sativus* (cucumber) or extract thereof; about 0.1%, w/w, *Calendula officinalis* (*calendula*) or extract thereof; about 0.1%, w/w, tocopherol; and *Helianthus annuus* (sunflower) seed oil q.s. to 100%.

The certified natural, fragrance-free diaper rash composition can (i) consist or consist essentially of certified natural and/or organic ingredients or (ii) be substantially free or devoid of synthetic ingredients that negate natural certification.

A method of treating or preventing dermatitis or diaper rash can comprise applying a certified natural, fragrance-free diaper rash composition of the present disclosure to a selected skin area having dermatitis or diaper rash and, optionally, leaving the certified natural diaper rash composition in contact with the selected skin are for a first period of time (e.g., at least 1 hour, etc.).

In a third aspect, a certified natural sunscreen composition, preferably for use in preventing or protecting against sunburn or overexposure to ultraviolet radiation, is disclosed.

The certified natural sunscreen composition can comprise zinc oxide, titanium dioxide, ethylhexyl palmitate, *Aloe vera* (juice) or extract thereof, lecithin, *Helianthus annuus* (sunflower) seed oil, sodium laurylglucosides hydroxypropylsulfonate, *Glycine soja* (soybean) oil, xanthan gum, phenoxyethanol, glycerin, *Prunus amygdalus dulcis* (sweet almond) oil, *Theobroma cacao* (cocoa) butter, *Sesamum indicum* (sesame) oil, *Camellia sinensis* (green tea) (leaf) or extract thereof, *Daucus carota* (carrot) or extract thereof, tocopherol, ethylhexylglycerin, and water.

The certified natural sunscreen composition can comprise 2-10%, w/w, zinc oxide; 2-10%, w/w, titanium dioxide; 2-12%, w/w, ethylhexyl palmitate; 2-10%, w/w, *Aloe vera* (juice) or extract thereof; 1-6%, w/w, lecithin; 0.05-5%, w/w, *Helianthus annuus* (sunflower) seed oil; 0.05-5%, w/w, sodium laurylglucosides hydroxypropylsulfonate; 0.05-5%, w/w, *Glycine soja* (soybean) oil; 0.05-5%, w/w, xanthan gum; 0.01-2%, w/w, phenoxyethanol; 0.01-2%, w/w, glycerin; 0.01-2%, w/w, *Prunus amygdalus dulcis* (sweet almond) oil; 0.01-2%, w/w, *Theobroma cacao* (cocoa) butter; 0.01-2%, w/w, *Sesamum indicum* (sesame) oil; 0.01-2%, w/w, *Camellia sinensis* (green tea) (leaf) or extract thereof; 0.01-2%, w/w, *Daucus carota* (carrot) or extract thereof; 0.01-2%, w/w, tocopherol; 0.01-1%, w/w, ethylhexylglycerin; and water q.s. to 100%.

The certified natural sunscreen composition can comprise about 6%, w/w, zinc oxide; about 6%, w/w, titanium dioxide; about 7.5%, w/w, ethylhexyl palmitate; about 6%, w/w, *Aloe vera* (juice) or extract thereof; about 3%, w/w, lecithin; about 2%, w/w, *Helianthus annuus* (sunflower) seed oil; about 1%, w/w, sodium laurylglucosides hydroxypropylsulfonate; about 1%, w/w, *Glycine soja* (soybean) oil; about 1.15%, w/w, xanthan gum; about 0.85%, w/w, phenoxyethanol; about 0.85%, w/w, glycerin; about 0.7%, w/w, *Prunus amygdalus dulcis* (sweet almond) oil; about 0.5%, w/w, *Theobroma cacao* (cocoa) butter; about 0.25%, w/w, *Sesamum indicum* (sesame) oil; about 0.25%, w/w, *Camellia sinensis* (green tea) (leaf) or extract thereof; about 0.2%, w/w, *Daucus carota* (carrot) or extract thereof; about 0.2%, w/w, tocopherol; about 0.1%, w/w, ethylhexylglycerin; and water q.s. to 100%.

The certified natural sunscreen composition can (i) consist or consist essentially of certified natural and/or organic ingredients or (ii) be substantially free or devoid of synthetic ingredients that negate natural certification.

A method of preventing or protecting against sunburn or overexposure to ultraviolet radiation can comprise applying a certified natural sunscreen composition of the present disclosure to a selected skin area prior to exposing said selected skin area to ultraviolet radiation and, optionally, leaving the certified natural sunscreen composition in contact with the selected skin are for a first period of time (e.g., during sun exposure, at least 1 hour, etc.).

In a third aspect, a certified natural sunscreen composition with natural sparkle or shimmer, preferably for use in preventing or protecting against sunburn or overexposure to ultraviolet radiation, is disclosed.

The certified natural sunscreen composition with natural sparkle or shimmer can comprise zinc oxide, titanium dioxide, ethylhexyl palmitate, *Aloe vera* (juice) or extract thereof, sodium laurylglucosides hydroxypropylsulfonate, lecithin, caprylic/capric triglyceride, cosmetic bioglitter, *Helianthus annuus* (sunflower) seed oil, xanthan gum, natural perfume or fragrance, glycerin, *Prunus amygdalus dulcis* (sweet almond) oil, gluconolactone, *Theobroma cacao* (cocoa) butter, sodium benzoate, *Sesamum indicum* (sesame)

oil, *Camellia sinensis* (green tea) (leaf) or extract thereof, *Daucus carota* (carrot) or extract thereof, tocopherol, methylcobalamin, and water.

The certified natural sunscreen composition with natural sparkle or shimmer can comprise 2-10%, w/w, zinc oxide; 2-10%, w/w, titanium dioxide; 1-12%, w/w, ethylhexyl palmitate; 1-10%, w/w, *Aloe vera* (juice) or extract thereof; 0.5-15%, w/w, sodium laurylglucosides hydroxypropylsulfonate; 1-6%, w/w, lecithin; 0.5-10%, w/w, caprylic/capric triglyceride; 0.5-5%, w/w, cosmetic bioglitter; 0.05-5%, w/w, *Helianthus annuus* (sunflower) seed oil; 0.05-5%, w/w, xanthan gum; 0.05-5%, w/w, natural perfume or fragrance; 0.01-3%, w/w, glycerin; 0.01-3%, w/w, *Prunus amygdalus dulcis* (sweet almond) oil; 0.01-3%, w/w, gluconolactone; 0.01-2%, w/w, *Theobroma cacao* (cocoa) butter; 0.01-2%, w/w, sodium benzoate; 0.01-2%, w/w, *Sesamum indicum* (sesame) oil; 0.01-2%, w/w, *Camellia sinensis* (green tea) (leaf) or extract thereof; 0.01-2%, w/w, *Daucus carota* (carrot) or extract thereof; 0.01-2%, w/w, tocopherol; 0.01-1%, w/w, methylcobalamin; and water q.s. to 100%.

The certified natural sunscreen composition with natural sparkle or shimmer can comprise about 6%, w/w, zinc oxide; about 6%, w/w, titanium dioxide; about 6-7.5%, w/w, ethylhexyl palmitate; about 2-5%, w/w, *Aloe vera* (juice) or extract thereof; about 5%, w/w, sodium laurylglucosides hydroxypropylsulfonate; about 3%, w/w, lecithin; about 2.5%, w/w, caprylic/capric triglyceride; about 2%, w/w, cosmetic bioglitter; about 1.3-2%, w/w, *Helianthus annuus* (sunflower) seed oil; about 1.12-1.15%, w/w, xanthan gum; about 1%, w/w, natural perfume or fragrance; about 0.6-0.85%, w/w, glycerin; about 0.7%, w/w, *Prunus amygdalus dulcis* (sweet almond) oil; about 0.6%, w/w, gluconolactone; about 0.2-0.5%, w/w, *Theobroma cacao* (cocoa) butter; about 0.3%, w/w, sodium benzoate; about 0.25%, w/w, *Sesamum indicum* (sesame) oil; about 0.19-0.25%, w/w, *Camellia sinensis* (green tea) (leaf) or extract thereof; about 0.1-0.2%, w/w, *Daucus carota* (carrot) or extract thereof; about 0.1-0.2%, w/w, tocopherol; about 0.05%, w/w, methylcobalamin; and water q.s. to 100%.

The certified natural sunscreen composition with natural sparkle or shimmer can (i) consist or consist essentially of certified natural and/or organic ingredients or (ii) be substantially free or devoid of synthetic ingredients that negate natural certification.

A method of preventing or protecting against sunburn or overexposure to ultraviolet radiation can comprise applying a certified natural sunscreen composition with natural sparkle or shimmer of the present disclosure to a selected skin area prior to exposing said selected skin area to ultraviolet radiation and, optionally, leaving the certified natural sunscreen composition with natural sparkle or shimmer in contact with the selected skin are for a first period of time (e.g., during sun exposure, at least 1 hour, etc.).

In a third aspect, a certified natural after-sun, tan-enhancing bronzer, skin toner or moisturizer composition with natural sparkle or shimmer, preferably for use in toning or moisturizer skin and/or enhancing skin pigmentation or tan after exposure to ultraviolet radiation, is disclosed.

The certified natural after-sun, tan-enhancing bronzer, skin toner or moisturizer composition with natural sparkle or shimmer can comprise *Aloe vera* (juice) or extract thereof, caprylic/capric triglyceride, cetearyl olivate, sorbitan olivate, cosmetic bioglitter, *Helianthus annuus* (sunflower) seed oil, propanediol, xanthan gum, natural perfume or fragrance, glycerin, tapioca starch, saccharide isomerate, caramel color, gluconolactone, hydroxyethyl cellulose, sodium benzoate, ascorbic acid, *Lavandula angustifolia* (lavender) oil, *Camellia sinensis* (green tea) (leaf) or extract thereof, tocopherol, jojoba esters, hyaluronic acid or sodium hyaluronate, and water.

The certified natural after-sun, tan-enhancing bronzer, skin toner or moisturizer composition with natural sparkle or shimmer can comprise 1-12%, w/w, *Aloe vera* (juice) or extract thereof; 0.5-10%, w/w, caprylic/capric triglyceride; 0.5-6%, w/w, cetearyl olivate; 0.5-6%, w/w, sorbitan olivate; 0.05-5%, w/w, cosmetic bioglitter; 0.5-6%, w/w, *Helianthus annuus* (sunflower) seed oil; 0.5-6%, w/w, propanediol; 0.01-2%, w/w, xanthan gum; 0.01-2%, w/w, natural perfume or fragrance; 0.5-6%, w/w, glycerin; 0.5-5%, w/w, tapioca starch; 0.05-5%, w/w, saccharide isomerate; 0.05-5%, w/w, caramel color; 0.05-2.5%, w/w, gluconolactone; 0.05-2.5%, w/w, hydroxyethyl cellulose; 0.05-2.5%, w/w, sodium benzoate; 0.05-2.5%, w/w, ascorbic acid; 0.05-2.5%, w/w, *Lavandula angustifolia* (lavender) oil; 0.01-2%, w/w, *Camellia sinensis* (green tea) (leaf) or extract thereof; 0.01-2%, w/w, tocopherol; 0.01-2%, w/w, jojoba esters; 0.01-2%, w/w, hyaluronic acid or sodium hyaluronate; and water q.s. to 100%.

The certified natural after-sun, tan-enhancing bronzer, skin toner or moisturizer composition with natural sparkle or shimmer can comprise about 6%, w/w, *Aloe vera* (juice) or extract thereof; about 3%, w/w, caprylic/capric triglyceride; about 2.5%, w/w, cetearyl olivate; about 2.5%, w/w, sorbitan olivate; about 1%, w/w, cosmetic bioglitter; about 2%, w/w, *Helianthus annuus* (sunflower) seed oil; about 2%, w/w, propanediol; about 0.1%, w/w, xanthan gum; about 0.35%, w/w, natural perfume or fragrance; about 2%, w/w, glycerin; about 1.5%, w/w, tapioca starch; about 1-1.5%, w/w, saccharide isomerate; about 1%, w/w, caramel color; about 0.6%, w/w, gluconolactone; about 0.4%, w/w, hydroxyethyl cellulose; about 0.35%, w/w, sodium benzoate; about 0.25%, w/w, ascorbic acid; about 0.25%, w/w, *Lavandula angustifolia* (lavender) oil; about 0.1-0.2%, w/w, *Camellia sinensis* (green tea) (leaf) or extract thereof; about 0.2-0.25%, w/w, tocopherol; about 0.2%, w/w, jojoba esters; about 0.2%, w/w, hyaluronic acid or sodium hyaluronate; and water q.s. to 100%.

The certified natural after-sun, tan-enhancing bronzer, skin toner or moisturizer composition with natural sparkle or shimmer can (i) consist or consist essentially of certified natural and/or organic ingredients or (ii) be substantially free or devoid of synthetic ingredients that negate natural certification.

A method of toning or moisturizer skin and/or enhancing skin pigmentation or tan after exposure to ultraviolet radiation can comprise applying a certified natural after-sun, tan-enhancing bronzer, skin toner or moisturizer composition with natural sparkle or shimmer of the present disclosure to a selected skin area prior to exposing said selected skin area to ultraviolet radiation and, optionally, leaving the certified natural after-sun, tan-enhancing bronzer, skin toner or moisturizer composition with natural sparkle or shimmer in contact with the selected skin are for a first period of time (e.g., at least 1 hour, etc.).

This summary is provided to introduce a selection of concepts in a simplified form that are further described below in the detailed description. This summary is not intended to identify key features or essential features of the claimed subject matter, nor is it intended to be used as an indication of the scope of the claimed subject matter.

Additional features and advantages of exemplary embodiments of the present disclosure will be set forth in the description which follows, and in part will be obvious from the description, or may be learned by the practice of such exemplary embodiments. The features and advantages of such embodiments may be realized and obtained by means of the instruments and combinations particularly pointed out in the appended claims. These and other features will become more fully apparent from the following description and appended claims, or may be learned by the practice of such exemplary embodiments as set forth hereinafter.

It is also noted that each of the foregoing, following, and/or other features described herein represent a distinct embodiment of the present disclosure. Moreover, combinations of any two or more of such features represent distinct embodiments of the present disclosure. Such embodiments can also be combined in any suitable combination and/or order without departing from the scope of this disclosure. Thus, each of the features described herein can be combinable with any one or more other features described herein in any suitable combination and/or order. Accordingly, the present disclosure is not limited to the specific combinations of exemplary embodiments described in detail herein.

DETAILED DESCRIPTION

Before describing various embodiments of the present disclosure in detail, it is to be understood that this disclosure is not limited to the specific parameters and description of the particularly exemplified systems, methods, and/or products that may vary from one embodiment to the next. Thus, while certain embodiments of the present disclosure will be described in detail, with reference to specific features (e.g., configurations, parameters, properties, steps, components, ingredients, members, elements, parts, and/or portions, etc.), the descriptions are illustrative and are not to be construed as limiting the scope of the present disclosure and/or the claimed invention. In addition, the terminology used herein is for the purpose of describing the embodiments, and is not necessarily intended to limit the scope of the present disclosure and/or the claimed invention.

While the detailed description is separated into sections, the section headers and contents within each section are not intended to be self-contained descriptions and embodiments. Rather, the contents of each section within the detailed description are intended to be read and understood as a collective whole where elements of one section may pertain to and/or inform other sections. Accordingly, embodiments specifically disclosed within one section may also relate to and/or serve as additional and/or alternative embodiments in another section having the same and/or similar systems, devices, methods, and/or terminology.

Abbreviated List of Defined Terms

To assist in understanding the scope and content of the foregoing and forthcoming written description and appended claims, a select few terms are defined directly below. Unless defined otherwise, all technical and scientific terms used herein have the same meaning as commonly understood by one of ordinary skill in the art to which the present disclosure pertains.

Unless defined otherwise, all technical and scientific terms used herein have the same meaning as commonly understood by one of ordinary skill in the art to which the present disclosure pertains.

The terms "comprising," "comprise," "comprises," and similar terms, as used herein, including in the claims, shall be inclusive and/or open-ended and do not exclude additional, un-recited elements or method steps, illustratively. Additionally, the terms to "including," "having," "involving," "containing," "characterized by," variants thereof (e.g., "includes," "has," and "involves," "contains," etc.), and similar terms as used herein, including the claims, shall be inclusive and/or open-ended, shall have the same meaning as the word "comprising" and variants thereof (e.g., "comprise" and "comprises"), and do not exclude additional, un-recited elements or method steps, illustratively.

As used herein, the transitional phrases "consisting of" "consist of" and similar terms shall be close-ended so as to exclude additional, un-recited elements or method steps, illustratively.

As used herein, the transitional phrase "consisting essentially of" means that the scope of a claim is to be interpreted to encompass the specified materials or steps recited in the claim, "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP § 2111.03. Thus, the term "consisting essentially of" when used in a claim of this disclosure is not intended to be interpreted to be equivalent to "comprising."

As used herein, the terms "about," "approximately," and similar terms, with regard to a value, mean+/−10% of the stated value or amount represented thereby. For instance, throughout the present disclosure, the term "about" is used in connection with a percent concentration or composition of a component or ingredient (e.g., in a composition, formulation, or mixture, such as a fluid or liquid mixture, aqueous mixture, solution, etc., optionally or preferably measured as a w/w percent, w/v percent, v/v percent, etc.). In such instance, the term "about" and/or the term "+/−10%" implies and/or includes +/−10% of the stated numeric value, as opposed to +/−10 percentage points of the recited percent. By way of example, where 20% w/w of a component or ingredient reflects 20 g of the component or ingredient per 100 mL of total mixture, the term "about" and/or the term "+/−10%" implies and/or includes a recited range from 18 g to 22 g (i.e., from 18% w/w to 22% w/w), not a range of 10% w/w to 30% w/w. Alternatives for so-called "about" values and/or +/−10% include +/−1%, +/−2%, +/−3%, +/−4%, +/−5%, +/−6%, +/−7%, +/−8%, or +/−9% of the stated value, each of which is contemplated as a suitable alternative to or substitute for the term "about" or the use of +/−10% herein.

It will also be appreciated that where two or more values, or a range of values (e.g., less than, greater than, at least, and/or up to a certain value, and/or between two recited values) is disclosed or recited, any specific value or range of values falling within the disclosed values or range of values is likewise disclosed and contemplated herein. Thus, disclosure of an illustrative measurement (e.g., volume, concentration, etc.) that is less than or equal to about 10 units or between 0 and 10 units includes, illustratively, a specific disclosure of: (i) a measurement of 9 units, 5 units, 1 units, or any other value between 0 and 10 units, including 0 units and/or 10 units; and/or (ii) a measurement between 9 units and 1 units, between 8 units and 2 units, between 6 units and 4 units, and/or any other range of values between 0 and 10 units.

As used herein, the term "substantially devoid," "substantially free," and similar terms mean (1) an undetectable or unquantifiable amount, (2) less than or below an amount generally considered by those skilled in the art to reflect a detectable or quantifiable amount, and/or (3) less than or below an amount generally considered by those skilled in the art to be functional or able to achieve a (desired or expected) result.

In at least one embodiment, the terms "form," "forming," and the like are open-ended, such that sub-components that (are combined, mixed, or included together so as to) form a component (e.g., system, application, product, composition, mixture, ingredient, element, part, etc.) do not necessarily constitute the entire component. Accordingly, a component can comprise said sub-components, without, necessarily, consisting, either entirely or essentially, of said sub-components, and a system or kit can comprise said components, without, necessarily, consisting, either entirely or essentially, of said components.

As used herein, the term "composition" includes products, formulations, and mixtures, as well as devices, apparatus, assemblies, kits, and so forth. Similarly, the term "method" includes processes, procedures, steps, and so forth. The terms "formulation" and "composition" may be used interchangeably herein, except where context clearly indicates otherwise.

As used herein, the term "method" also contemplates processes, procedures, steps, and so forth. Moreover, the term "products" also contemplates systems, compositions, kits, and so forth.

Various aspects of the present disclosure, including systems, methods, and/or products may be illustrated with reference to one or more embodiments or implementations, which are exemplary in nature. As used herein, the terms "embodiment" and implementation" mean "serving as an example, instance, or illustration," and should not necessarily be construed as preferred or advantageous over other aspects disclosed herein. In addition, reference to an "implementation" of the present disclosure or invention includes a specific reference to one or more embodiments thereof, and vice versa, and is intended to provide illustrative examples without limiting the scope of the invention, which is indicated by the appended claims rather than by the description thereof.

It is noted that embodiments of the present disclosure can comprise one or more combinations of two or more of the features described herein. As used herein, "feature(s)" and similar terms can include, for example, one or more compositions, ingredients, components, elements, members, parts, portions, systems, methods, steps, configurations, parameters, properties, or other aspect of the subject matter at hand. Embodiments can include any of the features, options, and/or possibilities set out elsewhere in the present disclosure, including in other aspects or embodiments of the present disclosure. It is also noted that while each of the foregoing, following, and/or other features described herein represents a distinct embodiment of the present disclosure, features can also be combined and/or combinable with another one or more other features in any suitable combination and/or order, with or without one or more additional features included therewith or performed therebetween, to form unique embodiments, each of which is contemplated in the present disclosure. Such combinations of any two or more of such features represent distinct embodiments of the present disclosure. Accordingly, the present disclosure is not limited to the specific combinations of exemplary embodiments described in detail herein and disclosure of certain features relative to a specific embodiment of the present disclosure should not be construed as limiting application or inclusion of said features to the specific embodiment.

In addition, unless a feature is described as being requiring in a particular embodiment, features described in the various embodiments can be optional and may not be included in other embodiments of the present disclosure. Moreover, unless a feature is described as requiring another feature in combination therewith, any feature herein may be combined with any other feature of a same or different embodiment disclosed herein. Likewise, any steps recited in any method described herein and/or recited in the claims can be executed in any suitable order and are not necessarily limited to the order described and/or recited, unless otherwise stated (explicitly or implicitly). Such steps can, however, also be required to be performed in a particular order in certain embodiments of the present disclosure.

As used throughout this application the words "can" and "may" are used in a permissive sense (i.e., meaning having the potential to), rather than the mandatory sense (i.e., meaning must).

The word "or" as used herein means any one member of a particular list and also includes any combination of members of that list.

As used in this specification and the appended claims, the singular forms "a," "an" and "the also contemplate plural referents, unless the context clearly dictates otherwise. Thus, for example, reference to a "moisturizer" includes one, two, or more moisturizers. Similarly, reference to a plurality of" referents should be interpreted as comprising a single referent and/or a plurality of referents unless the content and/or context clearly dictate otherwise. Thus, reference to "moisturizers" does not necessarily require a plurality of such moisturizers. Instead, it will be appreciated that independent of conjugation; one or more moisturizers are contemplated herein.

As used herein, the term "natural" refers to organic products, products derived from plants, minimally processed products generally known to be non-toxic for at least topical applications, and the like.

As used herein, the terms "mixture," "fluid mixture," "liquid mixture," and the like can comprise any suitable composition and/or combination of the specific components thereof. For instance, a fluid or liquid mixture can comprise a solution, suspension, colloid, emulsion, or other mixture of liquid and non-liquid components.

By "Quantum satis" (also referred to as "q.s." or "qs") is meant the amount that is enough. Accordingly, a component or ingredient "qs 100%," "provided at qs 100%," or "qs to 100%" indicates that the component or ingredient is provided or included in an amount sufficient to complete the composition or to bring the total (of all components, whether recited or not) to 100%. It is noted, however, that a (final) component or ingredient "qs 100%," "provided at qs 100%," or "qs to 100%" does not indicate that the mixture consists of, consists essentially of, or only contains the components listed or recited immediately before the "qs 100%" component. In other words, "qs 100%," and similar terms, is meant to be an open-ended expression indicating the source of the remainder, whatever that remainder may be.

To facilitate understanding, like references (i.e., like naming of components and/or elements) have been used, where possible, to designate like components and/or elements common to the written description and/or figures. Specific language will also be used herein to describe the exemplary embodiments. Nevertheless, it will be understood that no limitation of the scope of the disclosure is thereby intended. Rather, it is to be understood that the language used to describe the exemplary embodiments is illustrative only and is not to be construed as limiting the scope of the disclosure (unless such language is expressly described herein as essential).

The headings used herein are for organizational purposes only and are not meant to be used to limit the scope of the description or the claims.

Illustrative Embodiments

The following description of illustrative embodiments includes disclosure that is relevant to one or more aspects or embodiments of the present disclosure. Accordingly, some embodiments of the present disclosure can include the combination of elements or features disclosed in the following examples. It is noted, however, that various aspects or embodiments of the present disclosure need not, may not, or do not include each and every element or feature disclosed in a particular example. Indeed, certain aspects or embodiments may have fewer than all of the exemplary elements or features disclosed in connection with the following illustrative embodiments without departing from the scope of the present disclosure. In addition, some aspects or embodiments may include one or more elements or features disclosed in a separate aspect or embodiment. In other words, elements or features disclosed in one or more of the following examples can be included and/or incorporated into any one or more of the embodiments disclosed herein.

Without being bound by any theory, use of the words "natural" and "organic" in marketing, labeling, and advertising of personal skin care products is not regulated by the U.S. Food and Drug Administration (FDA). Accordingly, appearance of the words "natural" and "organic" on labels, advertisements, or marketing materials (e.g., videos, audio recordings, etc.) can be misleading and even lead to allergic reactions in customers with sensitive skin. For this reason, rigid certification, such as that provided by the Natural Products Association (NPA, U.S.A.)—the oldest and only non-profit organization that certifies personal care products as natural, is prestigious, if not essential. The NPA requires, for example, that at least 95% percent of the ingredients in the products are natural or have been derived from natural resources (excluding water), only 100 percent natural fragrances and colorants, the avoidance of ingredients with health risks, no animal testing, biodegradable or recycled material in the packaging, and a list of all ingredients on the package labels. Accordingly, the NPA has emerged as the gold-standard in providing certification of natural products that meet the rigid standards of the NPA.

Illustrative Natural Diaper Rash Compositions and Related Methods

Diaper rash, or (diaper) dermatitis, is a common form of inflamed skin experienced by infants and toddlers, though anyone who wears a diaper regularly can develop the condition. Diaper rash is often related to infrequently changed diapers, skin sensitivity and chafing. Diaper rash is characterized by red, irritated skin on the buttocks, thighs, and genitals. Currently, most popular over the counter remedies aim to treat the common causes of diaper rash—yeast and moisture. However, while these products may effectively remediate these problems, they typically incorporate chemicals that carry their own unpleasant side effects. For example, nystatin, a topical powder commonly used as an antifungal to treat skin infections caused by yeast, such as diaper rash, carries with its use the risk of side effects including skin irritation, itching, rash, burning, eczema, and redness. Other treatments use petroleum-derived ointments to soothe dry skin and form a barrier to help protect skin from constant exposure to moisture. However, petroleum-derived treatments are problematic if the skin is not properly dried or cleaned before treatment. If this occurs, bacteria and moisture can become trapped within the petroleum and cause serious infections. Furthermore, petroleum products are derived from an unsustainable and nonrenewable resource which causes adverse effects on the environment. Accordingly, there are a number of disadvantages with diaper rash treatments that can be addressed.

Various embodiments of the present disclosure include a natural diaper rash composition or treatment formulation (e.g., cream or lotion). The composition can have soothing properties that help to stop painful burning, itching, or cracking of the skin by hydrating and sealing moisture into skin. In some embodiments, the composition can help fight the source of infection by comprising anti-bacterial properties. The formulation may cool the skin upon contact, thereby providing instant relief. The formulation can have predominantly natural components, meaning the ingredients are minimally processed, are organically derived, and do not include common allergens or chemicals known to cause irritation.

In an embodiment, the formulation may comprise at least one antibacterial ingredient, one or more emollients, one or more skin conditioners, and one or more antioxidants. Some of the ingredients may perform multiple desired functions, for example an ingredient may act as both an antibacterial and as a skin conditioner.

In an embodiment, the active ingredient may comprise zinc oxide. Zinc oxide is a known skin protectant. The fine particles of zinc oxide have deodorizing and antibacterial properties and is used to treat a wide variety of skin conditions including dermatitis, itching due to eczema, diaper rash and acne. While zinc oxide typically appears white, nanoparticles may be used, which because of their size do not scatter light and therefore do not appear white. In some embodiments it may be advantageous to have a formulation that maintains a white color post application, while in other embodiments it might be preferred that the formulation appear colorless or clear once applied to the skin. In some embodiments, the zinc oxide may comprise 10-15 wt. % of the formulation, more preferably 12-16 wt. %, more preferably 12-20 wt. %.

Formulations of the present disclosure may include a number of emollients. Emollients may include creams, lotions, ointments and the like. Emollients help to keep the skin moist by reducing water loss. Natural emollients are not derived from petroleum or inorganic chemicals. Natural emollients may be plant extracts. Natural emollients in the diaper rash formulation of the present disclosure may include beeswax, *Helianthus Annuus* (Sunflower) Oil, *Cocos Nucifera* (Coconut) Oil, and the like. The amount and combination of emollients may be adjusted to achieve a desired thickness or viscosity of the formulation. In some embodiments the emollients may comprise 40-50 wt. % of the formulation, more preferably 45-55 wt. %, more preferably 50-60 wt. %, more preferably 55-65 wt. %. In some embodiments, *Helianthus Annuus* Oil may comprise 30-40 wt. % of the formulation, more preferably 35-45 wt. %. In some embodiments, *Cocos Nucifera* Oil may comprise 1-4 wt. % of the formulation, more preferably 2-5 wt. %. in some embodiments, Beeswax may comprise 1-10 wt. % of the formulation, more preferably 5-15% of the formulation.

Formulations of the present disclosure may include skin conditioning ingredients derived from natural sources such as plant extracts. Skin conditioning ingredients may have properties known to soothe and moisturize skin. Skin conditioning ingredients may include *Butyrospermun Parkii* (Shea) Butter, *Aloe Barbadensis* (leaf) (*Aloe Vera* Gel) Juice, *Glycyrrhiza Glabra* (Licorice) Extract, *Cucumis Sativus* (Cucumber) Extract, *Chamomilla Recutita* (Chamomile) Extract, *Calendula Officicinalis* Extract, *Lavandula Angustifolia* (Lavender) Oil, and the like. The amount and combination of moisturizing and skin soothing ingredients may be adjusted to achieve a desired consistency and/or effect. In some embodiments the skin conditioning ingredients may comprise 5-10 wt. % of the formulation, more preferably 8-13 wt. %, more preferably 10-15 wt. %, more preferably 15-20 wt. %, more preferably 20-25 wt. %, more preferably 25-30 wt. %, more preferably 30-35 wt. %.

In some embodiments, *Butyrospermun Parkii* Butter may comprise 1-10 wt. % of the formulation, more preferably 5-15 wt. %. In some embodiments, *Aloe Barbadensis* Leaf Juice may comprise 15-25 wt. % of the formulation, more preferably 20-30 wt. %. In some embodiments, *Glycyrrhiza Glabra* (Licorice) Extract may comprise 0.01-0.10 wt. % of the formulation, more preferably 0.05-0.15 wt. % of the formulation. In some embodiments, *Cucumis Sativus* (Cucumber) Extract may comprise 0.01-0.10 wt. % of the formulation, more preferably 0.05-0.15 wt. % of the formulation. In some embodiments, *Chamomilla Recutita* (Chamomile) Extract may comprise 0.01-0.10 wt. % of the formulation, more preferably 0.05-0.15 wt. % of the formulation. In some embodiments, *Calendula Officicinalis* Extract may comprise 0.01-0.10 wt. % of the formulation, more preferably 0.05-0.15 wt. % of the formulation. In some embodiments, *Lavandula Angustifolia* (Lavender) Oil may comprise 0.05-0.15 wt. % of the formulation, more preferably 14-21 wt. % of the formulation.

Formulations of the present disclosure may include antioxidant properties. Antioxidants remove potentially damaging oxidizing agents from living organisms. Antioxidants of the composition of the present disclosure may include enzymes, vitamin C, vitamin E, and beta carotene. tocopherol (Vitamin E) may be used in the present formulation as an antioxidant or skin-conditioning agent. Tocopherols and tocotrienols comprise vitamin E. Tocotrienols are present in seeds and fruit. Natural sources of tocopherols include sunflower, peanut, walnut, sesame, and olive oils. The amount of antioxidants comprising the formulation of the present disclosure may be adjusted to achieve a desired consistency and/or effect. In some embodiments the antioxidants may comprise 0.10-0.20 wt. % of the formulation, more preferably 0.15-0.25 wt. %, more preferably 0.20-0.30 wt. %, more preferably 0.25-0.35 wt. %, more preferably 0.30-0.40 wt. %, more preferably 0.35-0.45 wt. %, more preferably 0.40-0.50 wt. %, more preferably 0.45-0.55 wt. %.

Some embodiments can include a natural diaper rash treatment composition, comprising one or more antibacterial agent, one or more emollients, one or more skin conditioners, one or more antioxidants, and/or, optionally, one or more fragrances. In some embodiments, the one or more emollients, the one or more skin conditioners, the one or more antioxidants, and/or the one or more optional fragrances can be plant derived.

In some embodiments, the natural diaper rash treatment composition can be (specifically formulated to be) applied to a skin surface with dermatitis. In at least one embodiment, the composition can be colorless once applied to (and absorbed by) the skin (surface). Illustrative methods (of treating or preventing dermatitis) can include applying the natural diaper rash treatment composition to a skin surface (with dermatitis or at risk of developing dermatitis). Methods can also include leaving the natural diaper rash treatment composition in contact with the skin for a period of time.

Some of the properties of certain ingredients listed above are shown below in Table 1:

TABLE 1

| Name | Illustrative Function* |
|---|---|
| Zinc Oxide | Active ingredient. Has deodorizing and antibacterial properties. Used to treat and prevent minor skin irritations including diaper rash. |
| *Helianthus Annuus* (Sunflower) Oil | This oil is derived from the sunflower plant. These oils are used by a wide variety of products for their skin conditioning, occlusive, emollient, moisturizing, and other properties. |
| *Aloe Barbadensis* (leaf) (Aloe Vera Gel) Juice | *Aloe vera* is a succulent plant species of the genus *Aloe*. It grows wild in tropical climates all over the world and is cultivated for agricultural and medicinal uses. *Aloe vera* is typically used as a moisturizer and anti-irritant, and is commonly added to makeup, moisturizers, soaps, sunscreens, shaving cream, and shampoos. Use of topical *aloe vera* is not associated with significant side effects. |
| Beeswax (*cera alba*) | A natural was produced by honeybees of the genus *Apis*. Chemically, beeswax consists mainly of esters of fatty acids and various long-chain alcohols. Beeswax is edible, having similar negligible toxicity to plant waxes, and is approved for food use in most countries. Beeswax is used in lip balm, lip gloss, hand creams, salves, and moisturizers. |
| *Butyrospermun Parkii* (Shea) Butter | *Butyrospermum Parkii* (Shea) Butter is derived from the shea tree, *Butyrospermum parkii*, also called Vitellaria paradoxa. The following functions have been reported for shea butter: skin conditioning agent - miscellaneous, skin conditioning agent - occlusive, viscosity increasing agent - nonaqueous. The shea tree is native to Central Africa, where it is used as a source of vegetable oil. The oil from the fruit of the shea tree contains about 45-50% oleic acid, 30-41% stearic acid, 5-9% plamitic acid and 4-5% linoleic acid. |
| *Calendula Officinalis* Extract | *Calendula officinalis* is a plant known as pot marigold. It should not be confused with other types of plants more commonly known as marigold, such as those in the genus Tagetes. In cosmetics and personal care products, *Calendula Officinalis* Flower Extract functions as a skin conditioning agent - miscellaneous. *Calendula Officinalis* Flower Extract may also function as a fragrance ingredient. *Calendula officinalis* has been used orally and on the skin in traditional herbal medicine, often because of its reported |

TABLE 1-continued

| Name | Illustrative Function* |
| --- | --- |
| | anti-inflammatory activity. Important components of *Calendula officinalis* include triterpene saponins, flavonoids, and carotenoids, which give the flower the orange and yellow colors. |
| *Chamomilla Recutita* (Chamomile) Extract | *Chamomilla Recutita* (Matricaria) Flower Oil is also known as German chamomile oil. These ingredients function mostly as fragrance ingredients and skin conditioning agents in cosmetic products. |
| *Cocos Nucifera* (Coconut) Oil | Coconut Oil, also called *Cocos Nucifera* (Coconut) Oil, is a pale-yellow, semisolid, edible oil. Coconut Acid is a mixture of fatty acids derived from Coconut Oil. Coconut Oil is commonly used in cosmetics and personal care products. |
| *Cucumis Sativus* (Cucumber) Extract | *Cucumis sativus* (cucumber) fruit extract is used in cosmetics and personal care products due to its antioxidant, anti-inflammatory, and skin-conditioning properties. The cucumber (*Cucumis sativus*) is a member of the gourd family, Cucurbitaceae, which also includes pumpkin, zucchini, watermelon, and squash. Botanically speaking, cucumbers are actually fruits because they are the part of flowering plants that contain the seeds and are the means by which such plants disseminate those seeds. Cucumber fruit contains a wide variety of beneficial nutrients, such as vitamins, minerals, amino acids, phytosterols, phenolic acids, fatty acids, and cucurbitacins. The major constituents that provide skin benefits include ascorbic acid (vitamin C), beta carotene, polysaccharides, and vitamin K. |
| *Glycyrrhiza Glabra* (Licorice) Extract | Licorice is the root of the *Glycyrrhiza glabra* plant, an herbaceous perennial legume native to southern Europe and parts of Asia. A sweet flavor can be extracted from licorice root to be used in foods and candies. Furthermore, in traditional Chinese medicine, licorice is believed to "harmonize" the ingredients in a formula. It has also been used to treat a variety of ailments in Ayurvedic medicine. Licorice extract is considered as an effective agent for treatment of atopic dermatitis. |
| *Lavandula Angustifolia* (Lavender) Oil | This is an aromatic extract that contributes to the scent of the product and helps to condition the skin. |
| Tocopherol (Vitamin E) | Tocopherol, or vitamin E, a fat-soluble vitamin is a naturally occurring antioxidant which can be isolated from vegetable oil. When isolated, Tocopherol is a viscous oil that varies in color from yellow to brownish red. Rather than Tocopherol itself, synthetic esters of Tocopherol are often used in cosmetic and personal care products. These esters include, Tocopheryl Acetate, the acetic acid ester of Tocopherol. In cosmetics and personal care products, Tocopherol Acetate is used in the formulation of lipstick, eye shadow, blushers, face powders and foundations, moisturizers, skin care products, bath soaps and detergents, hair conditioners, and many other products. Tocopherol functions as an antioxidant and a skin-conditioning agent. Tocopherol, a fat-soluble vitamin, is found in vegetable fats and oils, dairy products, meat, eggs, cereals, nuts, and leafy green and yellow vegetables. It is usually present in these foods as mixtures of different forms: alpha-, beta-, gamma-, and delta-Tocopherol. The alpha form has the same biological activity as vitamin E. Tocopherols can be produced from vegetable oils or can be synthesized. |

At least one preferred embodiment includes a (certified) natural diaper rash composition, preferably for use in treating or preventing dermatitis or diaper rash. The composition can comprise one or more natural, organic, and/or plant-derived ingredients, such as zinc oxide, *Aloe vera* (leaf and/or juice) (extract), beeswax, *Butyrospermum Parkii* (shea) butter, *Cocos nucifera* (coconut) oil, *Lavandula angustifolia* (lavender) oil, *Cucumis sativus* (cucumber) (extract), *Glycyrrhiza glabra* (licorice) (extract), *Calendula officinalis* (calendula) (extract), tocopherol, *Chamomilla recutita* (chamomile) oil, and *Helianthus annuus* (sunflower) (seed) oil. Each of the foregoing ingredients can be acceptable under the rigid standard of the prestigious Natural Products Association (in appropriate amount(s), for some ingredients). Some embodiments can include or comprise each of the foregoing ingredients. Some embodiments can consist or consist essentially of each of the foregoing ingredients. Alternative embodiments can include or comprise fewer than all of the foregoing ingredients. Some embodiments can include or comprise a combination of two or more of the foregoing ingredients.

In some embodiments, the composition (i) consists (essentially) of certified natural and/or organic ingredients or (ii) is (substantially) free or devoid of synthetic ingredients that negate natural certification. In some embodiments, the composition can include (trace amount(s) of) one or more non-natural or synthetic ingredients, while still maintaining certified status. For instance, various natural ingredient extraction processes use chemicals that remain (in trace amounts) in the final, extracted plant product. Other naturally occurring, plant-based compounds are processed or altered during extraction, formulation, or processing, thereby becoming (technically) a non-natural compound. Moreover, a small amount of one or more non-natural or synthetic ingredient(s) may be included in one or more embodiments (e.g., preservatives, solvents, conditioning agents, etc.). Certification (e.g., as "natural" or "organic") may not be negated by such ingredients being included in compositions of the present disclosure.

In some embodiments, the (certified) natural diaper rash composition can include (about) 5-20%, w/w, zinc oxide, preferably about 12%, w/w, zinc oxide.

In some embodiments, the (certified) natural diaper rash composition can include (about) 10-30%, w/w, *Aloe vera* (juice) (extract), preferably about 20%, w/w, *Aloe vera* (juice) (extract).

In some embodiments, the (certified) natural diaper rash composition can include (about) 5-15%, w/w, beeswax, preferably about 11.5%, w/w, beeswax.

In some embodiments, the (certified) natural diaper rash composition can include (about) 5-15%, w/w, *Butyrospermum Parkii* (shea) (butter or extract), preferably about 11%, w/w, *Butyrospermum Parkii* (shea) (butter or extract).

In some embodiments, the (certified) natural diaper rash composition can include (about) 1-5%, w/w, *Cocos nucifera* (coconut) oil, preferably about 3%, w/w, *Cocos nucifera* (coconut) oil.

In some embodiments, the (certified) natural diaper rash composition can include (about) 0.01-1%, w/w, *Lavandula angustifolia* (lavender) oil, preferably about 0.2%, w/w, *Lavandula angustifolia* (lavender) oil.

In some embodiments, the (certified) natural diaper rash composition can include (about) 0.01-1%, w/w, *Cucumis sativus* (cucumber) (extract), preferably about 0.1%, w/w, *Cucumis sativus* (cucumber) (extract).

In some embodiments, the (certified) natural diaper rash composition can include (about) 0.01-1%, w/w, *Glycyrrhiza glabra* (licorice) (extract), preferably about 0.1%, w/w, *Glycyrrhiza glabra* (licorice) (extract).

In some embodiments, the (certified) natural diaper rash composition can include (about) 0.01-1%, w/w, *Calendula officinalis* (*calendula*) (extract), preferably about 0.1%, w/w, *Calendula officinalis* (*calendula*) (extract).

In some embodiments, the (certified) natural diaper rash composition can include (about) 0.01-1%, w/w, tocopherol, preferably about 0.1%, w/w, tocopherol.

In some embodiments, the (certified) natural diaper rash composition can include (about) 0.01-1%, w/w, *Chamomilla recutita* (chamomile) oil, preferably about 0.1%, w/w, *Chamomilla recutita* (chamomile) oil.

In some embodiments, the (certified) natural diaper rash composition can include *Helianthus annuus* (sunflower) seed oil, preferably q.s. to 100%.

In some embodiments, the (certified) natural diaper rash composition can be (substantially) free or devoid of one or more (e.g., all or any) irritating ingredients.

In some embodiments, the (certified) natural diaper rash composition can be (substantially) free or devoid of one or more (e.g., all or any) ingredients known to irritate a baby's sensitive skin.

In some embodiments, the (certified) natural diaper rash composition can be (substantially) free or devoid of one or more (e.g., all or any) ingredients that have been linked to allergic dermatitis.

In some embodiments, the (certified) natural diaper rash composition can be (substantially) free or devoid of one or more (e.g., all or any) artificial fragrances.

In some embodiments, the (certified) natural diaper rash composition can be (substantially) free or devoid of one or more (e.g., all or any) controversial preservatives.

In some embodiments, the (certified) natural diaper rash composition can be (substantially) free or devoid of one or more (e.g., all or any) artificial preservatives.

In some embodiments, the (certified) natural diaper rash composition can be (substantially) free or devoid of PABA.

In some embodiments, the (certified) natural diaper rash composition can be (substantially) free or devoid of petroleum.

In some embodiments, the (certified) natural diaper rash composition can be (substantially) free or devoid of parabens.

In some embodiments, the (certified) natural diaper rash composition can be (substantially) free or devoid of phthalates.

In some embodiments, the (certified) natural diaper rash composition can be (substantially) free or devoid of methylisothiazolinone.

In some embodiments, the (certified) natural diaper rash composition can be (substantially) free or devoid of methylchloroisothiazolinone.

In some embodiments, the (certified) natural diaper rash composition can be (substantially) free or devoid of tea tree oil.

In some embodiments, the (certified) natural diaper rash composition can be (substantially) free or devoid of lemongrass.

Figure 5:
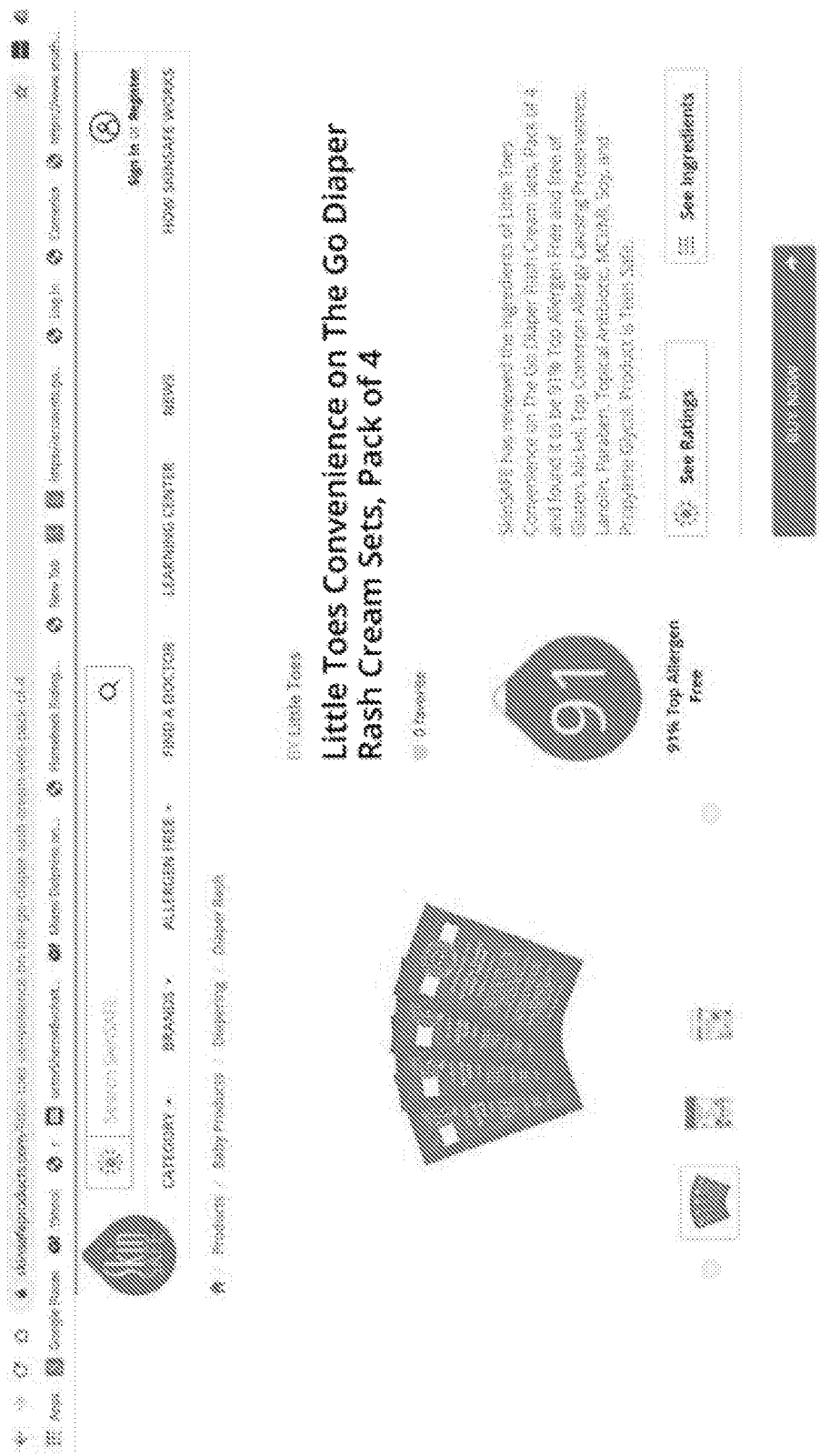
FIG. 5 is a copy of a webpage showing "SkinSAFE" certification of a Natural Diaper Rash Cream composition in accordance with one or more embodiments of the present disclosure.

Each of the natural diaper rash compositions, according to embodiments of the present disclosure have been certified and granted status as a "Certified Natural Personal Care Product" by the prestigious Natural Products Associate (NPA). See FIG. 1. The "Natural Seal" of the NPA sets the inventive compositions apart from other similar products in the art. Each of the natural diaper rash compositions, according to embodiments of the present disclosure have also been certified "SkinSAFE" and granted corresponding status. See FIG. 5. The "SkinSAFE" seal means that the SkinSAFE organization (a Mayo Clinic sponsored website) has reviewed the ingredients of the inventive natural diaper rash compositions and found them to be 91% Top Allergen Free and free of Gluten, Coconut, Nickel, Top Common Allergy Causing Preservatives, Lanolin, MCI/MI, Topical Antibiotic, Paraben, Soy, and Propylene Glycol. Thus, the "SkinSAFE" seal also sets the inventive compositions apart from other similar products in the art.

In some embodiments, the composition can be (substantially) free or devoid of fragrance(s). Illustratively, one or more embodiments of the present disclosure can be (substantially) free or devoid of *Lavandula angustifolia* (lavender) oil, *Glycyrrhiza glabra* (licorice) (extract), and/or *Chamomilla recutita* (chamomile) oil. Thus, at least one preferred embodiment includes a (certified) natural, fragrance-free diaper rash composition, preferably for use in treating or preventing dermatitis or diaper rash. In some embodiments, the composition can comprise one or more natural, organic, and/or plant-derived ingredients, such as zinc oxide, *Aloe vera* (extract), beeswax, *Butyrospermum Parkii* (shea) butter, *Cocos nucifera* (coconut) oil, *Cucumis sativus* (cucumber) (extract), *Calendula officinalis* (*calendula*) (extract), tocopherol, and *Helianthus annuus* (sunflower) (seed) oil. Each of the foregoing ingredients can be acceptable under the rigid standard of the prestigious Natural Products Association (in appropriate amount(s), for some ingredients). Some embodiments can include or comprise each of the foregoing ingredients. Some embodiments can consist or consist essentially of each of the foregoing ingredients. Alternative embodiments can include or comprise fewer than all of the foregoing ingredients. Some embodiments can include or comprise a combination of two or more of the foregoing ingredients.

In some embodiments, the composition (i) consists (essentially) of certified natural and/or organic ingredients or (ii) is (substantially) free or devoid of synthetic ingredients that negate natural certification. In some embodiments, the composition can include (trace amount(s) of) one or more non-natural or synthetic ingredients, while still maintaining certified status. For instance, various natural ingredient extraction processes use chemicals that remain (in trace amounts) in the final, extracted plant product. Other naturally occurring, plant-based compounds are processed or altered during extraction, formulation, or processing, thereby becoming (technically) a non-natural compound. Moreover, a small amount of one or more non-natural or synthetic ingredient(s) may be included in one or more embodiments (e.g., preservatives, solvents, conditioning agents, etc.). Certification (e.g., as "natural" or "organic") may not be negated by such ingredients being included in compositions of the present disclosure.

In some embodiments, the (certified) natural, fragrance-free diaper rash composition can include (about) 5-20%, w/w, zinc oxide, preferably about 12%, w/w, zinc oxide.

In some embodiments, the (certified) natural, fragrance-free diaper rash composition can include (about) 10-30%, w/w, *Aloe vera* (juice) (extract), preferably about 20%, w/w, *Aloe vera* (juice) (extract).

In some embodiments, the (certified) natural, fragrance-free diaper rash composition can include (about) 5-15%, w/w, beeswax, preferably about 11.5%, w/w, beeswax.

In some embodiments, the (certified) natural, fragrance-free diaper rash composition can include (about) 5-15%, w/w, *Butyrospermum Parkii* (shea) (butter or extract), preferably about 11%, w/w, *Butyrospermum Parkii* (shea) (butter or extract).

In some embodiments, the (certified) natural, fragrance-free diaper rash composition can include (about) 1-5%, w/w, *Cocos nucifera* (coconut) oil, preferably about 3%, w/w, *Cocos nucifera* (coconut) oil.

In some embodiments, the (certified) natural, fragrance-free diaper rash composition can include (about) 0.01-1%, w/w, *Cucumis sativus* (cucumber) (extract), preferably about 0.1%, w/w, *Cucumis sativus* (cucumber) (extract).

In some embodiments, the (certified) natural, fragrance-free diaper rash composition can include (about) 0.01-1%, w/w, *Calendula officinalis* (*calendula*) (extract), preferably about 0.1%, w/w, *Calendula officinalis* (*calendula*) (extract).

In some embodiments, the (certified) natural, fragrance-free diaper rash composition can include (about) 0.01-1%, w/w, tocopherol, preferably about 0.1%, w/w, tocopherol.

In some embodiments, the (certified) natural, fragrance-free diaper rash composition can include *Helianthus annuus* (sunflower) seed oil, preferably q.s. to 100%.

Figure 6:
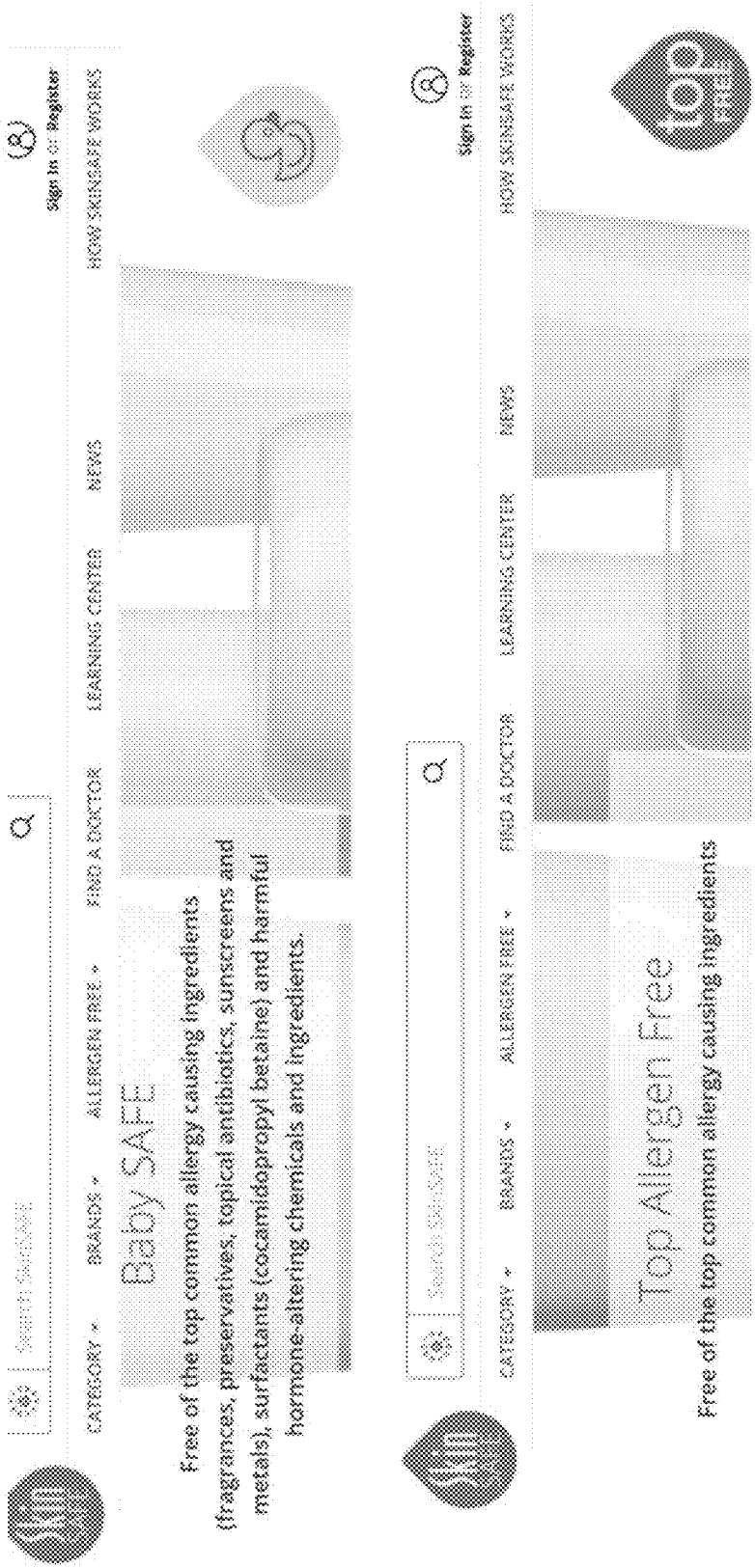
FIG. 6 is a copy of a webpage showing "SkinSAFE" certification for a Natural fragrance-free Diaper Rash Cream composition in accordance with one or more embodiments of the present disclosure.

Each of the natural, fragrance-free diaper rash compositions, according to embodiments of the present disclosure have been certified and granted status as a "Certified Natural Personal Care Product" by the prestigious Natural Products Associate (NPA). See FIG. 1. The "Natural Seal" of the NPA sets the inventive compositions apart from other similar products in the art. Each of the natural, fragrance-free diaper rash compositions, according to embodiments of the present disclosure have also been certified "SkinSAFE" and granted corresponding status. See FIG. 6. The "SkinSAFE" seal means that the SkinSAFE organization (a Mayo Clinic sponsored website) has reviewed the ingredients of the inventive natural, fragrance-free diaper rash compositions and found them to be 91% Top Allergen Free and free of Gluten, Coconut, Nickel, Top Common Allergy Causing Preservatives, Lanolin, MCI/MI, Topical Antibiotic, Paraben, Soy, and Propylene Glycol. Thus, the "SkinSAFE" seal also sets the inventive compositions apart from other similar products in the art.

Some embodiments can include a method of treating or preventing dermatitis or diaper rash. The method can comprise applying a composition of the present disclosure to a selected skin area having dermatitis or diaper rash, or at risk of developing dermatitis or diaper rash. An illustrative method or treating or preventing dermatitis or diaper rash can include (1) applying a natural diaper rash treatment (with or without fragrance, in accordance with an embodiment of the present disclosure) to a selected skin area, and (2) leaving the natural diaper rash treatment in contact with the skin for a first period of time.

In some embodiments the natural diaper rash treatment may be absorbed into the skin so that it is no longer visible on the surface of the skin. In other embodiments the natural diaper rash treatment may remain visible on the surface of the skin after it is applied. The natural diaper rash treatment may be applied to skin surface areas which typically experience dermatitis, particularly areas where the skin flexes, and areas that come into contact with moisture (e.g., urine). Areas where the skin typically flexes includes the elbows, behind the knees, and the front of the neck. Moisture prone areas may include areas commonly affected by diaper rash such as the thighs, buttocks, and genitals.

The natural diaper rash treatment may include at least one antibacterial ingredient, at least one emollient, at least one skin conditioner, and at least one antioxidant. All of the ingredients may be derived from plants, in some embodiments. In some embodiments, the antibacterial may comprise minerals such as zinc oxide, or the like. In some embodiments the natural diaper rash treatment may be in the form of a cream, balm, salve, ointment, or the like. High viscosity treatments may remain on the skin surface and form a barrier or protective layer to allow dermatitis afflicted skin to be healed while preventing additional moisture from coming into contact with the irritated skin. In other embodiments, it may be advantageous for the treatment to be absorbed into the skin to soothe and treat irritated skin. Additionally, it may be more comfortable for the treatment to be absorbed into the skin rather than remain on the surface. In some embodiments the treatment may be applied preemptively to prevent dermatitis from occurring.

Natural diaper rash treatments, compositions, or creams, in accordance with embodiments of the present disclosure, can soothe, moisturize, and protect baby's delicate skin in a natural way (e.g., at least by forming a moisture barrier). Unlike existing products that include petroleum, the inventive products can include zinc oxide (e.g., 12% zinc oxide), beeswax, and a combination of plant-based oils to create a moisture barrier. With the addition of shea butter to a mixture of sunflower, coconut and (optionally) lavender oil, along with Vitamin E (from tocopherol), the inventive diaper rash cream also soothes and moisturizes baby's sensitive skin.

The inventive diaper rash cream can be packaged in individual packets containing about 0.1-0.25 fluid ounces, preferably about 0.17 fluid ounce of the inventive formulation (e.g., for 'on the go' needs, as well as home use), reducing or eliminating the risk of bacteria and or mold build up.

Illustrative Natural Antioxidant Sunscreen Compositions and Related Methods

Our skin suffers a host of insults every day—age related damage, UV damage, pollution, oxidative damage, etc. In addition to being enjoyable, there are a multitude of benefits to your skin and your overall health that can be gained from sunscreen use. Sunscreen, also known as sun cream, sunblock, or suntan lotion, is a lotion, spray, gel foam, stick or other topical product that absorbs or reflects some of the sun's ultraviolet radiation and thus helps to protect against sunburn. Sunscreen protects your skin from the sun's harmful ultraviolet rays, which come in two forms—UVA and UVB. UVA rays are most commonly associated with skin aging, while UVB rays are the ones most commonly associated with sunburns. Both UVA and UVB rays are carcinogens. Anyone can get skin cancer regardless of age, gender or race. In fact, it is estimated that one in five Americans will develop skin cancer in their lifetime.

Most adults need to apply about one ounce of sunscreen to fully cover their body. When outdoors, sunscreen should be reapplied approximately every two hours, or after swimming or sweating. Chemical sunscreens which absorb into the skin contain one or more of the following active ingredients: oxybezone, avobenzone, octisalate, octocrylene, homosalate, and octinoxate. Recent studies by the FDA have found that the chemicals in sunscreen actually absorb beyond the skin and into the bloodstream. This study found that sunscreen users who applied the recommended amount per sun exposure time had blood stream concentrations of avobenzone, oxybenzone, octocrylene and ecamsule which far exceeded the FDA limit. High concentrations of oxybenzone were found in breast milk at concentrations exceeding 20 ng/mL seven days after completion of the study. Furthermore, oxybenzone is believed by scientists to have negative effects on human hormone levels and to be toxic to coral reefs which has led Hawaii to ban sunscreens that contain it.

Because skin cancer remains the most common cancer in the United States, and unprotected skin exposure to the sun's ultraviolet rays is a major risk factor in skin cancer, there is a need for alternative, non-toxic sunscreen formulations.

Disclosed herein is a natural antioxidant sunscreen. The natural antioxidant sunscreen formulation may include broad spectrum UVA and UVB sun protection, one or more humectant ingredients, one or more emollients, one or more occlusive ingredients, one or more skin conditioning agents, one or more antioxidants, one or more preservatives, one or more fragrances, and a solvent. In some embodiments, all of the ingredients of the sunscreen formulation may be non-toxic and derived from natural sources.

In an embodiment, a broad-spectrum composition comprising zinc oxide and/or titanium dioxide may be included to provide UVA and UVB protection. The embodiment may include a humectant component, an emollient component, an occlusive component, a skin conditioning component, an antioxidant component, a preservative component, and a solvent.

In another embodiment, a broad-spectrum composition may be increased to provide a higher level of sun protection factor. The sun protection factor may be rated to at least 30 SPF and above.

The term "broad spectrum" refers to protection against both UVA and UVB sun rays. Even with a high sun protection factor (SPF), sunscreens that are not broad spectrum will not protect a user from all UVA rays. The Current FDA SPF numbering system only identifies the amount of UVB protection a sunscreen product provides, not the amount of UVA protection. The broad-spectrum composition may comprise 10.0-15.0 wt. % of the total sunscreen formulation. The broad-spectrum composition of the natural antioxidant sunscreen may include titanium dioxide and/or zinc oxide. The titanium dioxide may comprise 3.0-8.0 wt. % of the total sunscreen composition. The zinc oxide may comprise 3.0-8.0 wt. % of the total sunscreen formulation. The amount of the broad-spectrum composition included in the sunscreen formulation may vary depending on the desired level of sun protection factor (SPF).

Natural antioxidant sunscreen formulations of the present disclosure may include a humectant. Humectants may be used to increase the solubility of the active ingredients to enhance the ability of the ingredients to penetrate the skin. The humectant may also counteract drying effects of other ingredients and help the skin retain moisture. Humectants in the disclosed sunscreen formulation may include gluconolactone and/or glycerin. The total amount of humectant in the sunscreen formulation may comprise 0.5-3.0 wt. % of the total sunscreen formulation. Glycerin may comprise 0.5-1.5 wt. % of the sunscreen formulation. Gluconolactone may comprise 0.5-1.5 wt. % of the sunscreen formulation.

Emollient preparations are used for protecting, moisturizing, and lubricating the skin. Emollients prevent water evaporation from the skin by forming an occlusive coating on the skin surface. The more lipid in the formulation, the greater emollient effect. In some embodiments, it may be advantageous for the sunscreen formulation to remain on the surface of the skin, thereby requiring a higher emollient content. In other embodiments it may be advantageous for the sunscreen formulation to be fully absorbed into the skin, as such, the emollient concentration may be lower. Emollients may comprise 5.0-15.0 wt. % of the sunscreen formulation of the present disclosure. Emollients may include ethylhexyl palmitate and/or lecithin. The emollients should be non-toxic and derived from natural sources. Lecithin may be present in a concentration of 1.0-6.0 wt. % of the sunscreen formulation. Ethylhexyl palmitate may be present in a concentration of 5.0-9.0 wt. % of the sunscreen formulation.

Occlusive agents physically prevent or retard water loss from the skin. Occlusive agents in sunscreen may be an effective way to trap humectants and emollients against the skin to allow the skin to remain soft and hydrated. Occlusive agents in the sunscreen formulation of the present disclosure may comprise 3.0-6.0 wt. % of the sunscreen formulation. Occlusive agents may include *Sesamum indicum* (sesame) oil, *Theobroma cacao* (cocoa) butter, *Prunus amygdalus dulcis* (sweet almond) oil, *Glycine soja* (soybean) oil, and *Helianthus annuus* (sunflower) oil. If included, *Sesamum indicum* (sesame) oil may comprise 0.1-1.0 wt. % of the sunscreen formulation. If included, *Theobroma cacao* (cocoa) butter may comprise 0.1-1.0 wt. % of the sunscreen formulation. If included, *Prunus amygdalus dulcis* (sweet almond) oil may comprise 0.1-1.0 wt. % of the sunscreen formulation. If included, *Glycine soja* (soybean) oil may comprise 0.5-1.5 wt. % of the sunscreen formulation. If included, *Helianthus annuus* (sunflower) oil may comprise 1.0-3.0 wt. % of the sunscreen formulation.

Skin conditioning agents provide a soft improved feel and texture to skin by providing skin with needed fats. This increases the moisture content of skin by reducing evaporation. Skin conditioning agents enhance the appearance of dry and damaged skin by reducing flaking and restoring skin elasticity. Skin conditioning agents may comprise 5.0-10.0 wt. % of the sunscreen formulation. Skin conditioning agents may include ethylhexylglycerin, *Aloe barbadensis* (leaf) juice, *Daucus carota* (carrot) extract, xanthan gum (corn sugar gum). Ethylhexylglycerin may be present in a concentration of 0.01-1.0 wt. % of the sunscreen formulation. *Aloe barbadensis* (leaf) juice may be present in a concentration of 4.0-8.0 wt. % of the sunscreen formulation. *Daucus carota* extract may be present in a concentration of 0.01-0.5 wt. % of the sunscreen formulation. Xanthan gum may be present in a concentration of 0.05-2.0 wt. % of the sunscreen formulation.

Antioxidants are natural substances made up of vitamins and minerals. Antioxidants may counter free radicals which damage DNA, lipids, and proteins by preventing or slowing the skin's deterioration due to a chemical reaction with oxygen. Antioxidants may also be considered skin conditioning agents. The antioxidants of the present formulation may include tocopherol (vitamin E) and *Camellia sinensis* (green tea) (leaf) extract. Antioxidants may comprise 0.1-1.0 wt. % of the sunscreen formulation. Tocopherol may comprise 0.01-1.0 wt. % of the sunscreen formulation. *Camellia sinensis* may comprise 0.1-0.5 wt. % of the sunscreen formulation.

Preservatives in the sunscreen formulation of the present disclosure are natural ingredients added to prevent spoilage of the sunscreen formulation. The preservatives of the sunscreen formulation may also provide fragrance. The sunscreen formulation of the present disclosure may contain 0.5-2.0 wt. % preservative. Preservatives may include phenoxyethanol and/or sodium benzoate. Phenoxyethanol may comprise 0.1-1.0 wt. % of the sunscreen formulation. Sodium benzoate may comprise 0.1-1.0 wt. % of the sunscreen formulation.

Solvents may be present in the sunscreen formulation of the present disclosure to dissolve other ingredients. Solvents may comprise 50.0-70.0 wt. % of the sunscreen formulation of the present disclosure. Suitable solvents may include any natural solvent such as aqua (purified water).

Some embodiments can include a natural antioxidant sunscreen, comprising a broad spectrum composition, preferably providing a sun protection factor (SPF) of at least 30 SPF, one or more humectant ingredients, one or more emollients, one or more occlusive, one or more skin conditioning agents, one or more antioxidants, one or more preservatives, one or more solvents, and/or, optionally, a perfume or fragrance. In some embodiments, substantially all of the ingredients of the natural antioxidant sunscreen are natural ingredients.

In some embodiments, the natural antioxidant sunscreen composition can be specifically formulated to be applied to a skin surface before exposure to sun or other forms of electromagnetic radiation, such as (artificial) light from UV lamps or bulbs (e.g., in tanning beds).

Additional properties of certain ingredients described herein (for the sunscreen formulation) are shown below in Table 2:

TABLE 2

| Name | Illustrative Function* |
| --- | --- |
| Water (aqua) | Water is used in the formulation of most types of cosmetic and personal care products. Water is primarily used as a solvent to dissolve many of the ingredients that impart skin benefits, such as conditioning agents and cleansing agents. Water also forms emulsions in which the oil and water components of the product are combined to form creams and lotions. Only Water that is free of toxins, pollutants and microbes is used in the formulation of cosmetics and personal care products. Water used for this purpose is also referred to as distilled water, purified water or aqua. |
| Phenoxyethanol | Phenoxyethanol is an oily, slightly viscous liquid with a faint rose-like odor. Phenoxyethanol prevents or retards microbial growth, and thus protects cosmetics and personal care products from spoilage. It may also be used in fragrances. Phenoxyethanol is usually synthesized for commercial use but it can also be found naturally in products such as green tea. |
| Lecithin | Lecithin is a naturally occurring mixture of the diglycerides of stearic, palmitic and oleic acids, linked to the choline ester of phosphoric acid whose form varies from a waxy mass to a thick, pourable liquid. Hydrogenated Lecithin is the product of controlled hydrogenation (addition of hydrogen) of Lecithin. Lecithin enhances the appearance of dry or damaged skin by reducing flaking and restoring suppleness. This ingredient also helps to form emulsions by reducing the surface tension of the substances to be emulsified Lecithin can be found in all living organisms and is a predominant component of nervous tissue. It can be obtained from soybean, corn, and egg yolks. Although Lecithin includes diglycerides of stearic, palmitic and oleic acids, the exact fatty acid composition of Lecithin varies depending on the source from which it was obtained. |
| Tocopherol | Tocopherol, or vitamin E, a fat-soluble vitamin is a naturally occurring antioxidant which can be isolated from vegetable oil. When isolated, Tocopherol is a viscous oil that varies in color from yellow to brownish red. Rather than Tocopherol itself, synthetic esters of Tocopherol are often used in cosmetic and personal care products. These esters include, Tocopheryl Acetate, the acetic acid ester of Tocopherol. In cosmetics and personal care products, Tocopherol Acetate is used in the formulation of lipstick, eye shadow, blushers, face powders and foundations, moisturizers, skin care products, bath soaps and detergents, hair conditioners, and many other products. Tocopherol functions as an antioxidant and a skin-conditioning agent. Tocopherol, a fat-soluble vitamin, is found in vegetable fats and oils, dairy products, meat, eggs, cereals, nuts, and leafy green and yellow vegetables. It is usually present in these foods |

TABLE 2-continued

| Name | Illustrative Function* |
|---|---|
| | as mixtures of different forms: alpha-, beta-, gamma-, and delta-Tocopherol. The alpha form has the same biological activity as vitamin E. Tocopherols can be produced from vegetable oils or can be synthesized. |
| Ethylhexylglycerin | Ethylhexylglycerin is an alkyl glyceryl ether. This means that the ethylhexyl group is bound to glycerin at one end by an ether linkage. The following functions have been reported for Ethylhexylglycerin: Deodorant agent, skin-conditioning agent - miscellaneous. The alkyl glyceryl ether ingredients, including Ethylhexylglycerin are solids at room temperature and are generally poorly soluble in water. Ethylhexylglycerin may enhance the function of preservatives by affecting the cell walls of bacteria promoting destruction of the bacteria by the preservative. |
| Titanium Dioxide | Naturally occurring oxide of titanium. Titanium oxide works as a UV filtering ingredient. |
| Zinc Oxide | Occurs naturally as the mineral zincite. Zinc oxide has deodorizing and antibacterial properties. Zinc oxide blocks both UVA and UVB rays of ultraviolet light. |
| Ethylhexyl Palmitate | Ethylhexyl palmitate is a mixture of esters formed by the reaction of 2-ethylhexyl alcohol with palmitic acid. It is typically used as a skin conditioning agent and/or emollient, and sometimes as a fragrance. |
| *Aloe Barbadensis* (leaf) (Aloe Vera Gel) Juice | This ingredient functions mostly as a skin conditioning agent. |
| *Helianthus Annuus* (Sunflower) Oil | This ingredient functions mostly as an occlusive. |
| *Glycine Soja* (Soybean) Oil | *Glycine Soja* is a plant derived oil used in cosmetic products for its skin conditioning, occlusive, emollient, and moisturizing properties. |
| Xanthan Gum | Xanthan Gum is a polysaccharide derived from the fermentation of carbohydrates. Xanthan Gum is derived from glucose or corn syrup. In cosmetics and personal care products, Xanthan Gum may function as a binder, emulsion stabilizer, skin-conditioning agent - miscellaneous, surfactant - emulsifying agent, or viscosity increasing agent - aqueous. Xanthan Gum is a very large molecule with an average molecular weight of 1,000,000 or more. Xanthan Gum dissolves readily in water with stirring, resulting in highly viscous solutions at low concentrations. |
| Glycerin | Glycerin is reported to function in cosmetics as a denaturant, fragrance ingredient, hair conditioning agent, humectant, oral care agent, oral health care drug, skin protectant, skin-conditioning agent, and viscosity decreasing agent. Glycerin is a clear, syrupy liquid. It can be in a crystallized state. Glycerin is completely miscible with water, methanol, ethanol, and the isomers of propanol, butanol, and pentanol. Natural glycerin is obtained as a by-product in the conversion of fats and oils into fatty acids or fatty acid methyl esters. |
| *Prunus Amygdalus Dulcis* (Sweet Almond) Oil | This ingredient functions mostly as an occlusive in this formulation. |
| Gluconolactone | This ingredient functions mostly as a humectant. |
| *Theobroma Cacao* (Cocoa) Butter | This ingredient functions mostly as an occlusive, though it may also function as a skin conditioning agent. |
| Sodium Benzoate | Sodium benzoate occurs naturally along with benzoic acid and its esters in many foods. Fruits and vegetables are rich sources. Other sources include seafood and dairy products. |
| *Camellia Sinensis* (Green Tea) (leaf) Extract | These ingredients function mostly as antioxidants and skin conditioning agents. The constituents of *C. sinensis* include amino acids, carotenoids, catechins, enzymes, flavonoids, and glycosides. The concentrations of these constituents in plants are influenced by growing conditions, geographical location, soil conditions, and processing. Generally recognized as safe (GRAS) for use in food products by the FDA. |
| *Sesamum Indicum* (Sesame) Oil | This ingredient functions mostly as an occlusive and may function as a skin conditioning agent. |
| *Daucus Carota* (Carrot) Extract | This ingredient functions mostly as a skin conditioning agent. |

At least one preferred embodiment includes a (certified) natural sunscreen composition, preferably for use in preventing or protecting against sunburn or overexposure to ultraviolet radiation. In some embodiments, the composition can comprise one or more natural, organic, and/or plant-derived ingredients, such as zinc oxide, titanium dioxide, ethylhexyl palmitate, *Aloe vera* (juice) extract, lecithin, *Helianthus annuus* (sunflower) seed oil, sodium laurylglucosides hydroxypropylsulfonate, *Glycine soja* (soybean) oil, xanthan gum, phenoxyethanol, glycerin, *Prunus amygdalus dulcis* (sweet almond) oil, *Theobroma cacao* (cocoa) butter, *Sesamum indicum* (sesame) oil, *Camellia sinensis* (green tea) (leaf) extract, *Daucus carota* (carrot) extract, tocopherol, ethylhexylglycerin, and water. Each of the foregoing ingredients can be acceptable under the rigid standard of the prestigious Natural Products Association (in appropriate amount(s), for some ingredients). Some embodiments can include or comprise each of the foregoing ingredients. Some embodiments can consist or consist essentially of each of the foregoing ingredients. Alternative embodiments can include or comprise fewer than all of the foregoing ingredients. Some embodiments can include or comprise a combination of two or more of the foregoing ingredients.

In some embodiments, the composition (i) consists (essentially) of certified natural and/or organic ingredients or (ii) is (substantially) free or devoid of synthetic ingredients that negate natural certification. In some embodiments, the composition can include (trace amount(s) of) one or more non-natural or synthetic ingredients, while still maintaining certified status. For instance, various natural ingredient extraction processes use chemicals that remain (in trace amounts) in the final, extracted plant product. Other naturally occurring, plant-based compounds are processed or altered during extraction, formulation, or processing, thereby becoming (technically) a non-natural compound. Moreover, a small amount of one or more non-natural or synthetic ingredient(s) may be included in one or more embodiments (e.g., preservatives, solvents, conditioning agents, etc.). Certification (e.g., as "natural" or "organic") may not be negated by such ingredients being included in compositions of the present disclosure.

In some embodiments, the (certified) natural sunscreen composition can include (about) 2-10%, w/w, zinc oxide, preferably about 6%, w/w, zinc oxide.

In some embodiments, the (certified) natural sunscreen composition can include (about) 2-10%, w/w, titanium dioxide, preferably about 6%, w/w, titanium dioxide.

In some embodiments, the (certified) natural sunscreen composition can include (about) 2-12%, w/w, ethylhexyl palmitate, preferably about 7.5%, w/w, ethylhexyl palmitate.

In some embodiments, the (certified) natural sunscreen composition can include (about) 2-10%, w/w, *Aloe vera* (juice) (extract), preferably about 6%, w/w, *Aloe vera* (juice) (extract).

In some embodiments, the (certified) natural sunscreen composition can include (about) 1-6%, w/w, lecithin, preferably about 3%, w/w, lecithin.

In some embodiments, the (certified) natural sunscreen composition can include (about) 0.05-5%, w/w, *Helianthus annuus* (sunflower) (seed) oil, preferably about 2%, w/w, *Helianthus annuus* (sunflower) (seed) oil.

In some embodiments, the (certified) natural sunscreen composition can include (about) 0.05-5%, w/w, sodium laurylglucosides hydroxypropylsulfonate, preferably about 1%, w/w, sodium laurylglucosides hydroxypropylsulfonate.

In some embodiments, the (certified) natural sunscreen composition can include (about) 0.05-5%, w/w, sodium laurylglucosides hydroxypropylsulfonate, preferably about 1%, w/w, sodium laurylglucosides hydroxypropylsulfonate.

In some embodiments, the (certified) natural sunscreen composition can include (about) 0.05-5%, w/w, xanthan gum, preferably about 1.15%, w/w, xanthan gum.

In some embodiments, the (certified) natural sunscreen composition can include (about) 0.01-2%, w/w, phenoxyethanol, preferably about 0.85%, w/w, phenoxyethanol. Some embodiments may be (substantially) free or devoid of phenoxyethanol.

In some embodiments, the (certified) natural sunscreen composition can include (about) 0.01-2%, w/w, glycerin, preferably about 0.85%, w/w, glycerin.

In some embodiments, the (certified) natural sunscreen composition can include (about) 0.01-2%, w/w, *Prunus amygdalus dulcis* (sweet almond) oil, preferably about 0.7%, w/w, *Prunus amygdalus dulcis* (sweet almond) oil.

In some embodiments, the (certified) natural sunscreen composition can include (about) 0.01-2%, w/w, *Theobroma cacao* (cocoa) butter, preferably about 0.5%, w/w, *Theobroma cacao* (cocoa) butter.

In some embodiments, the (certified) natural sunscreen composition can include (about) 0.01-2%, w/w, *Sesamum indicum* (sesame) oil, preferably about 0.25%, w/w, *Sesamum indicum* (sesame) oil.

In some embodiments, the (certified) natural sunscreen composition can include (about) 0.01-2%, w/w, *Camellia sinensis* (green tea) (leaf) extract, preferably about 0.25%, w/w, *Camellia sinensis* (green tea) (leaf) extract.

In some embodiments, the (certified) natural sunscreen composition can include (about) 0.01-2%, w/w, *Daucus carota* (carrot) extract, preferably about 0.2%, w/w, *Daucus carota* (carrot) extract.

In some embodiments, the (certified) natural sunscreen composition can include (about) 0.01-2%, w/w, tocopherol, preferably about 0.2%, w/w, tocopherol In some embodiments, the (certified) natural sunscreen composition can include (about) 0.01-1%, w/w, ethylhexylglycerin, preferably about 0.1%, w/w, ethylhexylglycerin. Some embodiments may be (substantially) free or devoid of ethylhexylglycerin.

In some embodiments, the (certified) natural sunscreen composition can include water, preferably q.s. to 100%.

Figure 2:
FIG. 2 is a copy of an actual, valid certification from the Natural Products Association of a Natural Sunscreen composition in accordance with one or more embodiments of the present disclosure.
Figure 7:
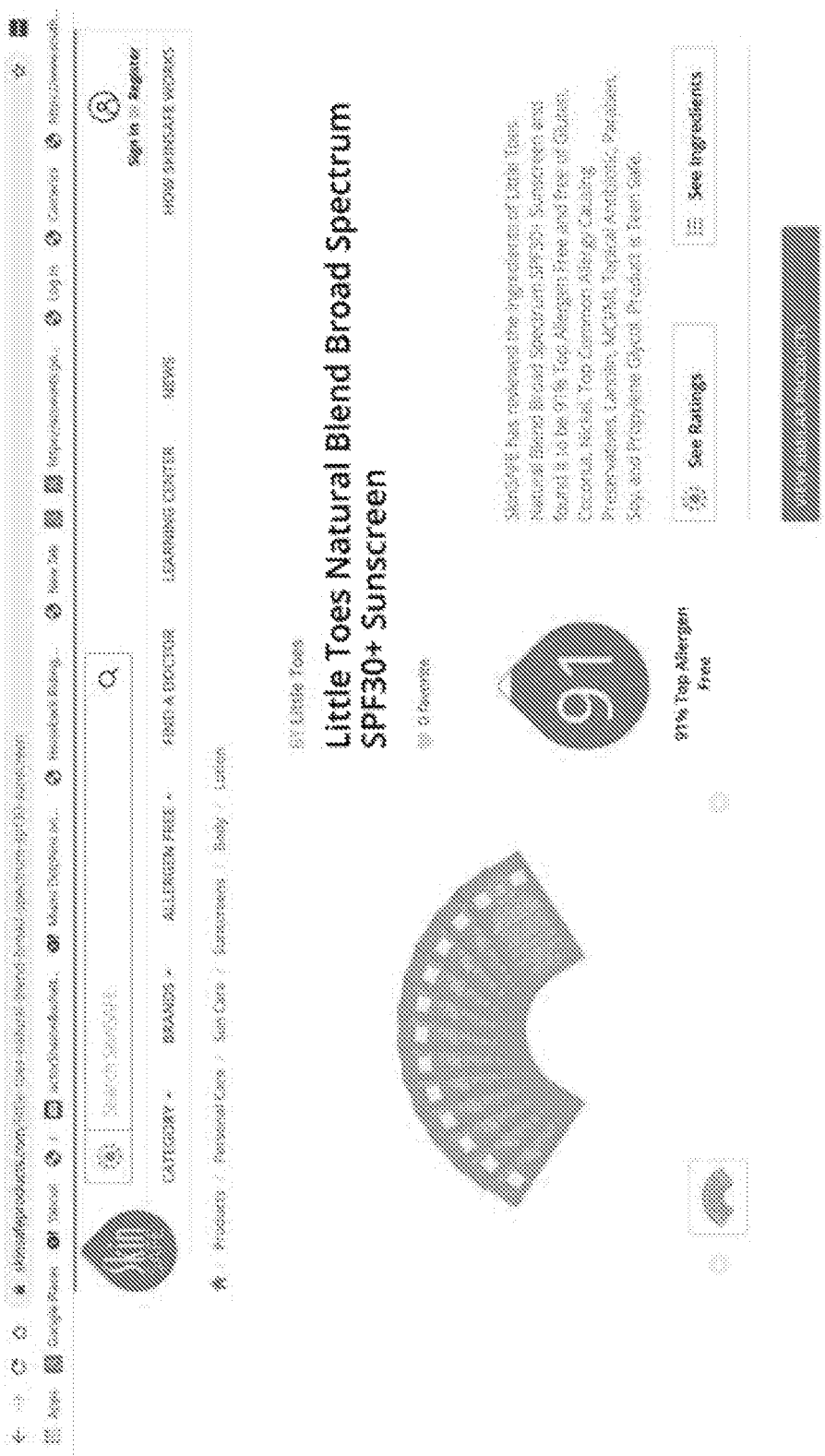
FIG. 7 is a copy of a webpage showing "SkinSAFE" certification of a Natural Sunscreen composition in accordance with one or more embodiments of the present disclosure.

Each of the natural sunscreen compositions, according to embodiments of the present disclosure have been certified and granted status as a "Certified Natural Personal Care Product" by the prestigious Natural Products Associate (NPA). See FIG. 2. The "Natural Seal" of the NPA sets the inventive compositions apart from other similar products in the art. Each of the natural sunscreen compositions, according to embodiments of the present disclosure have also been certified "SkinSAFE" and granted corresponding status. See FIG. 7. The "SkinSAFE" seal means that the SkinSAFE organization (a Mayo Clinic sponsored website) has reviewed the ingredients of the inventive natural sunscreen compositions and found them to be 91% Top Allergen Free and free of Gluten, Coconut, Nickel, Top Common Allergy Causing Preservatives, Lanolin, MCI/MI, Topical Antibiotic, Paraben, Soy, and Propylene Glycol. Thus, the "SkinSAFE" seal also sets the inventive compositions apart from other similar products in the art.

In some embodiments, the natural sunscreen composition can be specifically formulated to be applied to a skin surface before exposure to sun.

Some embodiments can include a method of preventing or protecting against sunburn or overexposure to ultraviolet radiation. The method can comprise applying a composition of the present disclosure to a selected skin area prior to exposure to ultraviolet radiation. An illustrative method or preventing or protecting against sunburn or overexposure to ultraviolet radiation can include (1) applying a natural sunscreen (in accordance with an embodiment of the present disclosure) to a selected skin area, and (2) leaving the natural sunscreen in contact with the skin area for a first period of time (e.g., during a period of exposure to ultraviolet radiation).

In some embodiments the natural sunscreen may be absorbed into the skin so that it is no longer visible on the surface of the skin. In other embodiments the natural sunscreen may remain visible on the surface of the skin after it is applied. The natural sunscreen may be applied to skin surface areas which typically experience sunburn, particularly areas where the skin experiences direct sunlight. Areas where the skin typically experiences sunburn or direct sunlight includes the face, forehead, neck, shoulders, arms, legs, feet, back, chest, stomach, and so forth.

Some screens and suntan lotions contain iridescent or shimmering qualities which give the user the appearance of glowing or sparkling skin in the sunlight. Many of these iridescent ingredients are derived from plastic sources and are not biodegradable and may be toxic to both the user and the environment.

Disclosed herein is a natural glitter sunscreen. The natural glitter sunscreen formulation may include broad spectrum UVA and UVB sun protection, a glitter ingredient, one or more humectant ingredients, one or more emollients, one or more occlusive ingredients, one or more skin conditioning agents, one or more antioxidants, one or more preservatives, one or more fragrances, and a solvent. In some embodiments, all of the ingredients of the sunscreen formulation may be non-toxic and derived from natural sources.

In an embodiment, a broad-spectrum composition comprising zinc oxide and/or titanium dioxide may be included to provide UVA and UVB protection. The embodiment may include a natural and/or bio glitter, to produce a sparkle effect. The embodiment may include a humectant component, an emollient component, an occlusive component, a skin conditioning component, an antioxidant component, a preservative component, and a solvent.

In another embodiment, a broad-spectrum composition may be increased to provide a higher level of sun protection factor. The sun protection factor may be rated to at least 30 SPF and above.

Natural glitter sunscreen formulations of the present disclosure may include a natural glitter ingredient made from non-toxic, natural, and/or biodegradable sources (e.g., a cosmetic bioglitter). For example, cosmetic bioglitter may be used. The natural glitter ingredient may comprise 1.0-5.0 wt. % of the natural glitter sunscreen formulation.

Natural glitter sunscreen formulations of the present disclosure may include a humectant. Humectants may be used to increase the solubility of the active ingredients to enhance the ability of the ingredients to penetrate the skin. The humectant may also counteract drying effects of other ingredients and help the skin retain moisture. Humectants in the disclosed sunscreen formulation may include gluconolactone and/or glycerin. The total amount of humectant in the sunscreen formulation may comprise 0.5-3.0 wt. % of the total sunscreen formulation. Glycerin may comprise 0.5-1.5 wt. % of the sunscreen formulation. Gluconolactone may comprise 0.5-1.5 wt. % of the sunscreen formulation.

Emollient preparations are used for protecting, moisturizing, and lubricating the skin. Emollients prevent water evaporation from the skin by forming an occlusive coating on the skin surface. The more lipid in the formulation, the greater emollient effect. In some embodiments, it may be advantageous for the sunscreen formulation to remain on the surface of the skin, thereby requiring a higher emollient content. In other embodiments it may be advantageous for the sunscreen formulation to be fully absorbed into the skin, as such, the emollient concentration may be lower. Emollients may comprise 5.0-15.0 wt. % of the sunscreen formulation of the present disclosure. Emollients may include ethylhexyl palmitate and/or lecithin. The emollients should be non-toxic and derived from natural sources. Lecithin may be present in a concentration of 1.0-6.0 wt. % of the sunscreen formulation. Ethylhexyl palmitate may be present in a concentration of 5.0-9.0 wt. % of the sunscreen formulation.

Occlusive agents physically prevent or retard water loss from the skin. Occlusive agents in sunscreen may be an effective way to trap humectants and emollients against the skin to allow the skin to remain soft and hydrated. Occlusive agents in the sunscreen formulation of the present disclosure may comprise 3.0-6.0 wt. % of the sunscreen formulation. Occlusive agents may include *Sesamum indicum* (sesame) oil, *Theobroma cacao* (cocoa) butter, *Prunus amygdalus dulcis* (sweet almond) oil, *Glycine soja* (soybean) oil, and *Helianthus annuus* (sunflower) oil. If included, *Sesamum indicum* (sesame) oil may comprise 0.1-1.0 wt. % of the sunscreen formulation. If included, *Theobroma cacao* (cocoa) butter may comprise 0.1-1.0 wt. % of the sunscreen formulation. If included, *Prunus amygdalus dulcis* (sweet almond) oil may comprise 0.1-1.0 wt. % of the sunscreen formulation. If included, *Glycine soja* (soybean) oil may comprise 0.5-1.5 wt. % of the sunscreen formulation. If included, *Helianthus annuus* (sunflower) oil may comprise 1.0-3.0 wt. % of the sunscreen formulation.

Skin conditioning agents provide a soft improved feel and texture to skin by providing skin with needed fats. This increases the moisture content of skin by reducing evaporation. Skin conditioning agents enhance the appearance of dry and damaged skin by reducing flaking and restoring skin elasticity. Skin conditioning agents may comprise 5.0-10.0 wt. % of the sunscreen formulation. Skin conditioning agents may include calcium gluconate, *Aloe barbadensis* (leaf) juice, *Daucus carota* (carrot) extract, xanthan gum (corn sugar gum). Calcium gluconate may be present in a concentration of 0.01-1.0 wt. % of the sunscreen formulation. *Aloe barbadensis* (leaf) juice may be present in a concentration of 4.0-8.0 wt. % of the sunscreen formulation. *Daucus carota* extract may be present in a concentration of 0.01-0.5 wt. % of the sunscreen formulation. Xanthan gum may be present in a concentration of 0.05-2.0 wt. % of the sunscreen formulation.

Antioxidants are natural substances made up of vitamins and minerals. Antioxidants may counter free radicals which damage DNA, lipids, and proteins by preventing or slowing the skin's deterioration due to a chemical reaction with oxygen. Antioxidants may also be considered skin conditioning agents. The antioxidants of the present formulation may include tocopherol (vitamin E), methylcobalamin (vitamin B12), and *Camellia sinensis* (green tea) (leaf) extract. Antioxidants may comprise 0.1-1.0 wt. % of the sunscreen formulation. Tocopherol may comprise 0.01-1.0 wt. % of the sunscreen formulation. Methylcobalamin may comprise 0.01-0.50 wt. % of the sunscreen formulation. *Camellia sinensis* may comprise 0.1-0.5 wt. % of the sunscreen formulation.

Preservatives in the sunscreen formulation of the present disclosure are natural ingredients added to prevent spoilage of the sunscreen formulation. The preservatives of the sunscreen formulation may also provide fragrance. The sunscreen formulation of the present disclosure may contain 0.5-2.0 wt. % preservative. Preservatives may include sodium benzoate. Sodium benzoate may comprise 0.1-1.0 wt. % of the sunscreen formulation.

Solvents may be present in the sunscreen formulation of the present disclosure to dissolve other ingredients. Solvents may comprise 50.0-70.0 wt. % of the sunscreen formulation of the present disclosure. In some embodiments, solvents may comprise quantum satis (Q.S.) as necessary for the sunscreen formulation to achieve the desired consistency. Suitable solvents may include any natural solvent such as aqua (deionized water).

Some embodiments can include a natural glitter sunscreen, comprising a broad spectrum composition, preferably providing a sun protection factor (SPF) of at least 30 SPF, a natural bioglitter ingredient, one or more humectant ingredients, one or more emollients, one or more occlusive, one or more skin conditioning agents, one or more antioxidants, one or more preservatives, one or more solvents, and/or, optionally, one or more fragrances. In some embodiments, substantially all of the ingredients or active ingredients of the natural glitter sunscreen are natural ingredients.

In some embodiments, the natural glitter sunscreen composition can be specifically formulated to be applied to a skin surface before exposure to sun.

Additional properties of certain ingredients described herein (for the sunscreen formulation) are shown below in Table 3:

TABLE 3

| Name | Illustrative Function* |
| --- | --- |
| Water (aqua) | Water is used in the formulation of most types of cosmetic and personal care products. Water is primarily used as a solvent to dissolve many of the ingredients that impart skin benefits, such as conditioning agents and cleansing agents. Water also forms emulsions in which the oil and water components of the product are combined to form creams and lotions. Only Water that is free of toxins, pollutants and microbes is used in the formulation of cosmetics and personal care products. Water used for this purpose is also referred to as distilled water, purified water or aqua. |
| Lecithin | Lecithin is a naturally occurring mixture of the diglycerides of stearic, palmitic and oleic acids, linked to the choline ester of phosphoric acid whose form varies from a waxy mass to a thick, pourable liquid. Hydrogenated Lecithin is the product of controlled hydrogenation (addition of hydrogen) of Lecithin. Lecithin enhances the appearance of dry or damaged skin by reducing flaking and restoring suppleness. This ingredient also helps to form emulsions by reducing the surface tension of the substances to be emulsified. Lecithin can be found in all living organisms and is a predominant component of nervous tissue. It can be obtained from soybean, corn, and egg yolks. Although Lecithin includes diglycerides of stearic, palmitic and oleic acids, the exact fatty acid composition of Lecithin varies depending on the source from which it was obtained. |
| Tocopherol | Tocopherol, or vitamin E, a fat-soluble vitamin is a naturally occurring antioxidant which can be isolated from vegetable oil. When isolated, Tocopherol is a viscous oil that varies in color from yellow to brownish red. Rather than Tocopherol itself, synthetic esters of Tocopherol are often used in cosmetic and personal care products. These esters include, Tocopheryl Acetate, the acetic acid ester of Tocopherol. In cosmetics and personal care products, Tocopherol Acetate is used in the formulation of lipstick, eye shadow, blushers, face powders and foundations, moisturizers, skin care products, bath soaps and detergents, hair conditioners, and many other products. Tocopherol functions as an antioxidant and a skin-conditioning agent. Tocopherol, a fat-soluble vitamin, is found in vegetable fats and oils, dairy products, meat, eggs, cereals, nuts, and leafy green and yellow vegetables. It is usually present in these foods as mixtures of different forms: alpha-, beta-, gamma-, and delta-Tocopherol. The alpha form has the same biological activity as vitamin E. Tocopherols can be produced from vegetable oils or can be synthesized. |
| Titanium Dioxide | Naturally occurring oxide of titanium. Titanium oxide works as a UV filtering ingredient. |
| Zinc Oxide | Occurs naturally as the mineral zincite. Zinc oxide has deodorizing and antibacterial properties. Zinc oxide blocks both UVA and UVB rays of ultraviolet light. |
| Ethylhexyl Palmitate | Ethylhexyl palmitate is a mixture of esters formed by the reaction of 2-ethylhexyl alcohol with palmitic acid. It is typically used as a skin conditioning agent and/or emollient, and sometimes as a fragrance. |
| *Aloe Barbadensis* (leaf) (Aloe Vera Gel) Juice | This ingredient functions mostly as a skin conditioning agent. |
| *Helianthus Annuus* (Sunflower) Oil | This ingredient functions mostly as an occlusive. |
| *Glycine Soja* (Soybean) Oil | *Glycine Soja* is a plant derived oil used in cosmetic products for its skin conditioning, occlusive, emollient, and moisturizing properties. |
| Xanthan Gum | Xanthan Gum is a polysaccharide derived from the fermentation of carbohydrates. Xanthan Gum is derived from glucose or corn syrup. in cosmetics and personal care products, Xanthan Gum may function as a binder, emulsion stabilizer, skin-conditioning |

TABLE 3-continued

| Name | Illustrative Function* |
|---|---|
| | agent - miscellaneous, surfactant - emulsifying agent, or viscosity increasing agent - aqueous. Xanthan Gum is a very large molecule with an average molecular weight of 1,000,000 or more. Xanthan Gum dissolves readily in water with stirring, resulting in highly viscous solutions at low concentrations. |
| Glycerin | Glycerin is reported to function in cosmetics as a denaturant, fragrance ingredient, hair conditioning agent, humectant, oral care agent, oral health care drug, skin protectant, skin-conditioning agent, and viscosity decreasing agent. Glycerin is a clear, syrupy liquid. It can be in a crystallized state. Glycerin is completely miscible with water, methanol, ethanol, and the isomers of propanol, butanol, and pentanol. Natural glycerin is obtained as a by-product in the conversion of fats and oils into fatty acids or fatty acid methyl esters. |
| *Prunus Amygdalus Dulcis* (Sweet Almond) Oil | This ingredient functions mostly as an occlusive in this formulation. Though it may act as a |
| Gluconolactone | This ingredient functions mostly as a humectant. |
| *Theobroma Cacao* (Cocoa) Butter | This ingredient functions mostly as an occlusive, though it may also function as a skin conditioning agent. |
| Sodium Benzoate | Sodium benzoate occurs naturally along with benzoic acid and its esters in many foods. Fruits and vegetables are rich sources Other sources include seafood and dairy products. |
| *Camellia Sinensis* (Green Tea) (leaf) Extract | These ingredients function mostly as antioxidants and skin conditioning agents. The constituents of *C. sinensis* include amino acids, carotenoids, catechins, enzymes, flavonoids, and glycosides. The concentrations of these constituents in plants are influenced by growing conditions, geographical location, soil conditions, and processing. Generally recognized as safe (GRAS) for use in food products by the FDA. |
| *Sesamum Indicum* (Sesame) Oil | This ingredient functions mostly as an occlusive and may function as a skin conditioning agent. |
| *Daucus Carota* (Carrot) Extract | This ingredient functions mostly as a skin conditioning agent. |
| Calcium Gluconate | This ingredient is the calcium salt of gluconic acid. Typically used as a chelating agent or skin conditioning agent. |
| bioGlitter | |
| Methylcobalamin (Vitamin B12) | |

At least one preferred embodiment includes a (certified) natural sunscreen composition with natural sparkle or shimmer, preferably for use in preventing or protecting against sunburn or overexposure to ultraviolet radiation. In some embodiments, the composition can comprise one or more natural, organic, and/or plant-derived ingredients, such as zinc oxide, titanium dioxide, ethylhexyl palmitate, *Aloe vera* (juice) (extract), sodium laurylglucosides hydroxypropylsulfonate, lecithin, caprylic/capric triglyceride, cosmetic bioglitter, *Helianthus annuus* (sunflower) seed oil, xanthan gum, natural perfume or fragrance, glycerin, *Prunus amygdalus dulcis* (sweet almond) oil, gluconolactone, *Theobroma cacao* (cocoa) butter, sodium benzoate, *Sesamum indicum* (sesame) oil, to *Camellia sinensis* (green tea) (leaf) (extract), *Daucus carota* (carrot) (extract), tocopherol, methylcobalamin, and water. Each of the foregoing ingredients can be acceptable under the rigid standard of the prestigious Natural Products Association (in appropriate amount(s), for some ingredients). Some embodiments can include or comprise each of the foregoing ingredients. Some embodiments can consist or consist essentially of each of the foregoing ingredients. Alternative embodiments can include or comprise fewer than all of the foregoing ingredients. Some embodiments can include or comprise a combination of two or more of the foregoing ingredients.

In some embodiments, the composition (i) consists (essentially) of certified natural and/or organic ingredients or (ii) is (substantially) free or devoid of synthetic ingredients that negate natural certification. In some embodiments, the composition can include (trace amount(s) of) one or more non-natural or synthetic ingredients, while still maintaining certified status. For instance, various natural ingredient extraction processes use chemicals that remain (in trace amounts) in the final, extracted plant product. Other naturally occurring, plant-based compounds are processed or altered during extraction, formulation, or processing, thereby becoming (technically) a non-natural compound. Moreover, a small amount of one or more non-natural or synthetic ingredient(s) may be included in one or more embodiments (e.g., preservatives, solvents, conditioning agents, etc.). Certification (e.g., as "natural" or "organic") may not be negated by such ingredients being included in compositions of the present disclosure.

In some embodiments, the (certified) natural sunscreen composition with natural sparkle or shimmer can include (about) 2-10%, w/w, zinc oxide, preferably about 6%, w/w, zinc oxide.

In some embodiments, the (certified) natural sunscreen composition with natural sparkle or shimmer can include (about) 2-10%, w/w, titanium dioxide, preferably about 6%, w/w, titanium dioxide.

In some embodiments, the (certified) natural sunscreen composition with natural sparkle or shimmer can include (about) 1-12%, w/w, ethylhexyl palmitate, preferably about 6-7.5%, w/w, ethylhexyl palmitate.

In some embodiments, the (certified) natural sunscreen composition with natural sparkle or shimmer can include (about) 1-10%, w/w, *Aloe vera* (juice) extract, preferably about 2-5%, w/w, *Aloe vera* (juice) extract.

In some embodiments, the (certified) natural sunscreen composition with natural sparkle or shimmer can include (about) 0.5-15%, w/w, sodium laurylglucosides hydroxypropylsulfonate, preferably about 5%, w/w, sodium laurylglucosides hydroxypropyl sulfonate.

In some embodiments, the (certified) natural sunscreen composition with natural sparkle or shimmer can include (about) 1-6%, w/w, lecithin, preferably about 3%, w/w, lecithin.

In some embodiments, the (certified) natural sunscreen composition with natural sparkle or shimmer can include (about) 0.5-10%, w/w, caprylic/capric triglyceride, preferably about 2.5%, w/w, caprylic/capric triglyceride.

In some embodiments, the (certified) natural sunscreen composition with natural sparkle or shimmer can include (about) 0.5-5%, w/w, cosmetic bioglitter, preferably about 2%, w/w, cosmetic bioglitter.

In some embodiments, the (certified) natural sunscreen composition with natural sparkle or shimmer can include (about) 0.05-5%, w/w, *Helianthus annuus* (sunflower) seed oil, preferably about 1.3-2%, w/w, *Helianthus annuus* (sunflower) seed oil.

In some embodiments, the (certified) natural sunscreen composition with natural sparkle or shimmer can include (about) 0.05-5%, w/w, xanthan gum, preferably about 1.12-1.15%, w/w, xanthan gum.

In some embodiments, the (certified) natural sunscreen composition with natural sparkle or shimmer can include (about) 0.05-5%, w/w, natural perfume or fragrance, preferably about 1%, w/w, natural perfume or fragrance.

In some embodiments, the (certified) natural sunscreen composition with natural sparkle or shimmer can include (about) 0.01-3%, w/w, glycerin, preferably about 0.6-0.85%, w/w, glycerin.

In some embodiments, the (certified) natural sunscreen composition with natural sparkle or shimmer can include (about) 0.01-3%, w/w, *Prunus amygdalus dulcis* (sweet almond) oil, preferably about 0.7%, w/w, *Prunus amygdalus dulcis* (sweet almond) oil.

In some embodiments, the (certified) natural sunscreen composition with natural sparkle or shimmer can include (about) 0.01-3%, w/w, gluconolactone, preferably about 0.6%, w/w, gluconolactone.

In some embodiments, the (certified) natural sunscreen composition with natural sparkle or shimmer can include (about) 0.01-2%, w/w, *Theobroma cacao* (cocoa) butter, preferably about 0.2-0.5%, w/w, *Theobroma cacao* (cocoa) butter.

In some embodiments, the (certified) natural sunscreen composition with natural sparkle or shimmer can include (about) 0.01-2%, w/w, sodium benzoate, preferably about 0.3%, w/w, sodium benzoate. Some embodiments may be (substantially) free or devoid of sodium benzoate.

In some embodiments, the (certified) natural sunscreen composition with natural sparkle or shimmer can include (about) 0.01-2%, w/w, *Sesamum indicum* (sesame) oil, preferably about 0.25%, w/w, *Sesamum indicum* (sesame) oil.

In some embodiments, the (certified) natural sunscreen composition with natural sparkle or shimmer can include (about) 0.01-2%, w/w, *Camellia sinensis* (green tea) (leaf) extract, preferably about 0.19-0.25%, w/w, *Camellia sinensis* (green tea) (leaf) extract.

In some embodiments, the (certified) natural sunscreen composition with natural sparkle or shimmer can include (about) 0.01-2%, w/w, *Daucus carota* (carrot) extract, preferably about 0.1-0.2%, w/w, *Daucus carota* (carrot) extract.

In some embodiments, the (certified) natural sunscreen composition with natural sparkle or shimmer can include (about) 0.01-2%, w/w, tocopherol, preferably about 0.1-0.2%, w/w, tocopherol.

In some embodiments, the (certified) natural sunscreen composition with natural sparkle or shimmer can include (about) 0.01-1%, w/w, methylcobalamin, preferably about 0.05%, w/w, methylcobalamin.

In some embodiments, the (certified) natural sunscreen composition with natural sparkle or shimmer can include water, preferably q.s. to 100%.

Figure 3:
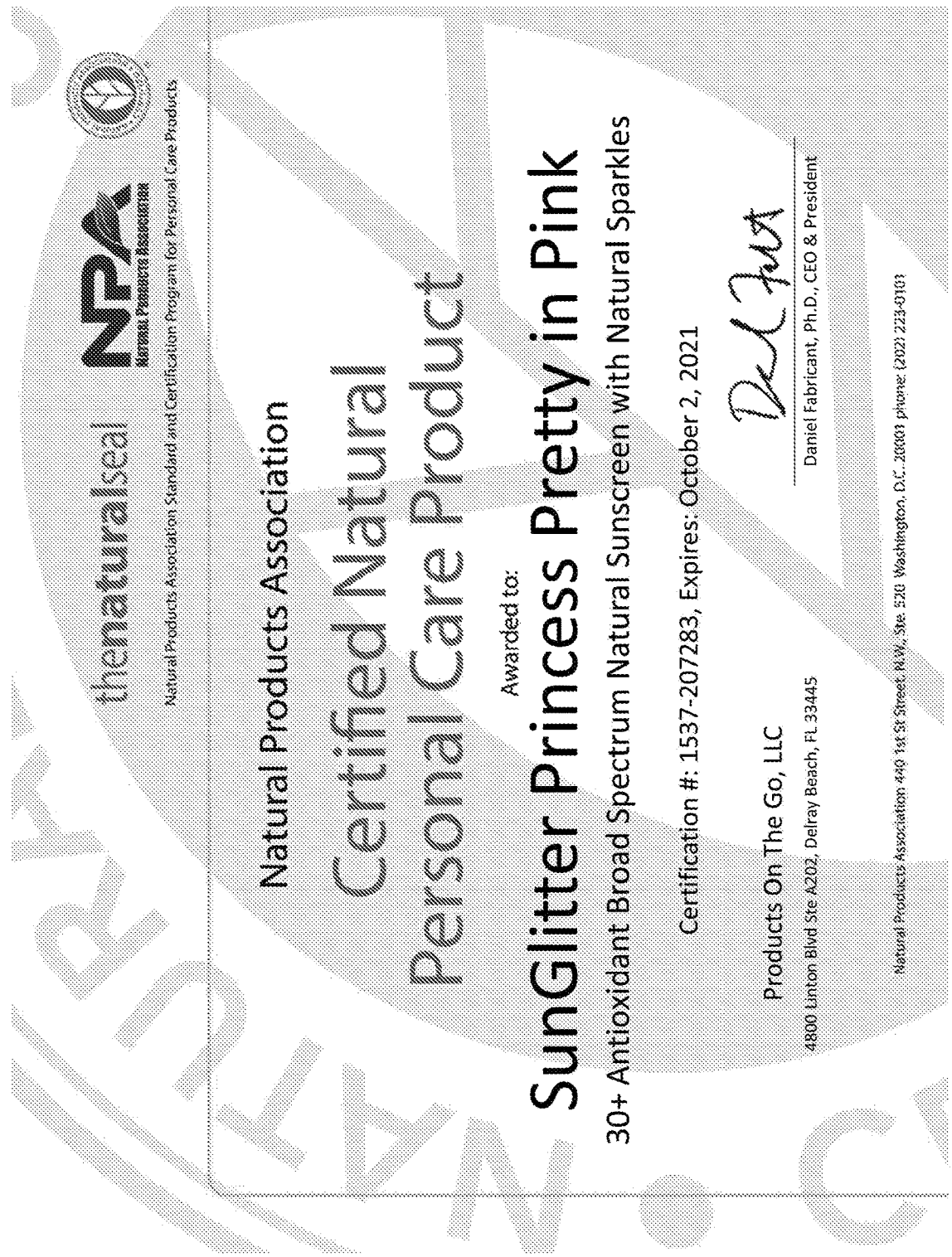
FIG. 3 is a copy of an actual, valid certification from the Natural Products Association of a Natural Sunscreen with Natural Sparkles composition in accordance with one or more embodiments of the present disclosure.

Each of the natural sunscreen composition with natural sparkle or shimmer, according to embodiments of the present disclosure have been certified and granted status as a "Certified Natural Personal Care Product" by the prestigious Natural Products Associate (NPA). See FIG. 3. The "Natural Seal" of the NPA sets the inventive compositions apart from other similar products in the art.

Some embodiments can include a method of preventing or protecting against sunburn or overexposure to ultraviolet radiation. The method can comprise applying a composition of the present disclosure to a selected skin area prior to exposure to ultraviolet radiation. An illustrative method or preventing or protecting against sunburn or overexposure to ultraviolet radiation can include (1) applying a natural sunscreen (in accordance with an embodiment of the present disclosure) to a selected skin area, and (2) leaving the natural sunscreen in contact with the skin area for a first period of time (e.g., during a period of exposure to ultraviolet radiation).

In some embodiments the natural sunscreen may be absorbed into the skin so that it is no longer visible on the surface of the skin. In other embodiments the natural sunscreen may remain visible on the surface of the skin after it is applied. The natural sunscreen may be applied to skin surface areas which typically experience sunburn, particularly areas where the skin experiences direct sunlight. Areas where the skin typically experiences sunburn or direct sunlight includes the face, forehead, neck, shoulders, arms, legs, feet, back, chest, stomach, and so forth.

Illustrative Natural Sparkle Bronzer/Moisturizer Compositions and Related Methods Our skin suffers a host of insults every day—age related damage, UV damage, pollution, oxidative damage, etc. In addition to being enjoyable, there are a multitude of benefits to your skin and your overall health that can be gained from after-sun creams and from foregoing suntanning altogether. It is estimated that one in five Americans will develop skin cancer in their lifetime, with prolonged, unprotected sun exposure being the primary cause. The sun's rays come in two damaging forms: UVA rays are most commonly associated with skin aging, while UVB rays are the ones most commonly associated with sunburns. Both UVA and UVB rays are carcinogens. Anyone can get skin cancer regardless of age, gender or race.

After-sun lotions, creams, gels, and other topical applications are crucial for rehydrating sunbaked skin to prevent drying and wrinkling, and in some cases to soothe impending burns. In some cases, bronzers may be added to after-sun lotions to help sunbathers achieve the desired bronze color, without spending copious amounts of time in the sun. Individuals may also use bronzers to achieve a tanned appearance without subject their skin to the sun's harmful rays.

Some suntan lotions contain iridescent or shimmering qualities which give the user the appearance of glowing or sparkling skin in the sunlight. Many of these iridescent ingredients are derived from plastic sources and are not biodegradable and may be toxic to both the user and the environment. Similarly, many ingredients in bronzing products are both toxic and harmful to the environment. For example, oxybenzone, found in bronzer has been found to act like estrogen in the body and has been linked to endometriosis in women. The FDA has linked parabens, commonly found in makeup, moisturizers, and spray tan products, to breast cancer, skin cancer, and decreased sperm count.

Disclosed herein is a natural sparkle bronzer. The natural sparkle bronzer formulation may include a humectant component, a glitter component, an occlusive component, a skin conditioning component, an antioxidant component, a preservative component, and a solvent component, a viscosity controlling component, an emulsifying component, and a colorant component.

In an embodiment, the natural sparkle bronzer formulation may include a humectant component, an occlusive component, a glitter component (e.g., a natural and/or bioglitter), a skin conditioning component, an antioxidant component, a preservative component, and a solvent component, a viscosity controlling component, an emulsifying component, and a colorant component.

In another embodiment, the natural sparkle bronzer formulation may include a fragrance, a humectant component, an occlusive component, a glitter component, a skin conditioning component, an antioxidant component, a preservative component, and a solvent component, a viscosity controlling component, an emulsifying component, and a colorant component.

In another embodiment, all of the ingredients of the natural sparkle bronzer formulation may be derived from natural sources. Naturally sourced and/or plant-derived ingredients are generally non-toxic ingredients which are safe for human use, and do not include plastics or other materials which are not biodegradable.

The natural sparkle bronzer formulations of the present disclosure may include a humectant. humectant component. Humectants may be used to increase the solubility of the active ingredients to enhance the ability of the ingredients to penetrate the skin. The humectant may also counteract drying effects of other ingredients and help the skin retain moisture. Humectants in the disclosed bronzer formulation may include gluconolactone and/or glycerin. The total amount of humectant in the bronzer formulation may comprise 3.0-6.0 wt. % of the total bronzer formulation. Glycerin may comprise 1.0-3.0 wt. % of the bronzer formulation. Gluconolactone may comprise 0.5-1.5 wt. % of the bronzer formulation. Saccharide isomerate may comprise 0.5-2.0 wt. % of the bronzer formulation. Hyaluronic acid may comprise 0.01-0.50 wt. % of the bronzer formulation.

Occlusive agents physically prevent or retard water loss from the skin. Occlusive agents in the bronzer formulation may be an effective way to trap humectants and emollients against the skin to allow the skin to remain soft and hydrated. Occlusive agents in the bronzer formulation may include *Helianthus annuus* (sunflower) oil, caprylic/capric triglyceride, and/or hydrolyzed jojoba esters. Occlusive agents in the bronzer formulation of the present disclosure may comprise 6.0-10.0 wt. % of the bronzer formulation. *Helianthus annuus* oil may comprise 1.0-4.0 wt. % of the bronzer formulation. Caprylic/capric triglyceride may comprise 2.0-5.0 wt. % of the bronzer formulation. Hydrolyzed jojoba esters (jojoba esters) may comprise 0.1-1.0 wt. % of the bronzer formulation.

Skin conditioning agents provide a soft improved feel and texture to skin by providing skin with needed fats. This increases the moisture content of skin by reducing evaporation. Skin conditioning agents enhance the appearance of dry and damaged skin by reducing flaking and restoring skin elasticity. Skin conditioning agents may include *Aloe barbadensis* (leaf) (*Aloe vera* gel) juice, cetearyl olivate, xanthan gum (corn sugar gum), and/or *Lavandula* (lavender) *angustifolia* oil. Skin conditioning agents may comprise 10.0-16.0 wt. % of the bronzer formulation. *Aloe barbadensis* (leaf) juice may comprise 3.0-8.0 wt. % of the bronzer formulation. Cetearyl olivate may comprise 1.0-4.0 wt. % of the bronzer formulation. Xanthan gum may comprise 0.01-0.30 wt. % of the bronzer formulation. *Lavandula angustifolia* oil may comprise 0.01-0.40 wt. % of the bronzer formulation.

Antioxidants are natural substances made up of vitamins and minerals. Antioxidants may counter free radicals which damage DNA, lipids, and proteins by preventing or slowing the skin's deterioration due to a chemical reaction with oxygen. Antioxidants may also be considered skin conditioning agents. The antioxidants of the present formulation may include tocopherol (vitamin E), ascorbic acid (vitamin C), and/or *Camellia sinensis* (green tea) (leaf) extract. Antioxidants may comprise 1.0-3.0 wt. % of the bronzer formulation. Tocopherol may comprise 0.01-0.50 wt. % of the bronzer formulation. Ascorbic acid may comprise 0.01-0.50 wt. % of the formulation. *Camellia sinensis* (leaf) extract may comprise 0.01-0.50 wt. % of the bronzer formulation.

Preservatives in the bronzer formulation of the present disclosure are natural ingredients added to prevent spoilage of the bronzer formulation. The preservatives of the bronzer formulation may also provide fragrance. The bronzer formulation of the present disclosure may contain sodium benzoate and/or parfum. Preservative may comprise 0.5-1.0 wt. % of the bronzer formulation. Sodium benzoate may comprise 0.1-0.5 wt. % of the bronzer formulation. Parfum may comprise 0.1-0.5 wt. % of the bronzer formulation.

Solvents may be present in the bronzer formulation of the present disclosure to dissolve other ingredients. Solvents may comprise aqua (purified or deionized water). In some embodiments, the amount of solvent may be used quantum satis. In other embodiments, the solvent may comprise 50.0-70.0 wt. % of the bronzer formulation.

Viscosity controlling ingredients or thickening agents may be present in the bronzer formulation to increase the viscosity of the formulation. They may also improve the suspension of other ingredients and improve the stability of an emulsion. Viscosity controlling ingredients in the bronzer formulation may include sodium polymethacrylate, propanediol, tapioca starch, and/or hydroxyethylcellulose. Propanediol may be comprised of Zemea® (corn) Propanediol. Viscosity controlling ingredients may comprise 1.0-8.0 wt. % of the bronzer formulation. Tapioca starch may comprise 0.5-2.5 wt. % of the bronzer formulation. Hydroxyethylcellulose may comprise 0.2-0.6 wt. % of the bronzer formulation. Sodium polymethacrylate may comprise 1.0-2.0 wt. % of the bronzer formulation. Propanediol may comprise 1.0-5.0 wt. % of the bronzer formulation.

Other ingredients in the bronzer formulation may be included to provide emulsifying effects and or coloration. These ingredients may include sorbitan olivate, an emulsifying agent, in an amount comprising 1.5-4.0 wt. % of the bronzer formulation. These ingredients may also include caramel or caramel color, a sugary material obtained from heating sucrose or glucose solutions which may be used as a colorant for the bronzer base. The caramel color may comprise 0.5-2.0 wt. % of the bronzer formulation.

In some embodiments, glitter material may be added to the bronzer formulation to produce a sparkle or shimmer effect. The glitter may be derived from a natural source and/or may be non-toxic and/or biodegradable. Adequate glitter may include cosmetic bioglitter. Glitter, including bioglitter, may comprise 0.5-2.0 wt. % of the bronzer formulation.

Some embodiments can include a natural sparkle bronzer, comprising a natural bioglitter ingredient, one or more humectant ingredients, one or more emollients, one or more occlusive, one or more skin conditioning agents, one or more antioxidants, one or more preservatives, one or more viscosity controlling ingredients, one or more emulsifying ingredients, one or more colorant ingredients, one or more solvents, and/or, optionally, one or more fragrances. In some embodiments, all of the ingredients of the natural sparkle bronzer can be natural ingredients.

Illustratively, the natural sparkle bronzer formulation can be specifically formulated to be applied to a skin surface before and/or after exposure to sun.

Additional properties of certain ingredients described herein (for the bronzer formulation) are shown below in Table 4:

TABLE 4

| Name | Illustrative Function* |
|---|---|
| Water (aqua) | Water is used in the formulation of most types of cosmetic and personal care products. Water is primarily used as a solvent to dissolve many of the ingredients that impart skin benefits, such as conditioning agents and cleansing agents. Water also forms emulsions in which the oil and water components of the product are combined to form creams and lotions. Only Water that is free of toxins, pollutants and microbes is used in the formulation of cosmetics and personal care products. Water used for this purpose is also referred to as distilled water, purified water or aqua. |
| Tocopherol | Tocopherol, or vitamin E, a fat-soluble vitamin is a naturally occurring antioxidant which can be isolated from vegetable oil. When isolated, Tocopherol is a viscous oil that varies in color from yellow to brownish red. Rather than Tocopherol itself, synthetic esters of Tocopherol are often used in cosmetic and personal care products. These esters include, Tocopheryl Acetate, the acetic acid ester of Tocopherol. In cosmetics and personal care products, Tocopherol Acetate is used in the formulation of lipstick, eye shadow, blushers, face powders and foundations, moisturizers, skin care products, bath soaps and detergents, hair conditioners, and many other products. Tocopherol functions as an antioxidant and a skin-conditioning agent. Tocopherol, a fat-soluble vitamin, is found in vegetable fats and oils, dairy products, meat, eggs, cereals, nuts, and leafy green and yellow vegetables. It is usually present in these foods as mixtures of different forms: alpha-, beta-, gamma-, and delta-Tocopherol. The alpha form has the same biological activity as vitamin E. Tocopherols can be produced from vegetable oils or can be synthesized. |
| Cetearyl Olivate | This is the ester of cetearyl alcohol and the fatty acids derived from olive oil. Used as a conditioning agent. |
| Sorbitan Olivate | This is the monoester of the fatty acids derived from olive oil and hexitol anhydrides derived from sorbitol. This is typically used as a surfactant or emulsifying agent. |
| Caprylic/Capric Triglyceride | This ingredient is manufactured by hydrolyzing coconut oil, removing the free glycerin, and separating the medium chain length fatty acids by fractional distillation. The acids are then blended in the proper ratio and re-esterfied with glycerin. Typically used as a fragrance ingredient, skin conditioning agent, occlusive, and solvent. |
| (Zemea ® (corn)) Propanediol | This ingredient is used in cosmetics as a solvent and/or viscosity decreasing agent. May also be used as a humectant, emollient, preservative booster, and carrier for cosmetic ingredients. |
| *Aloe Barbadensis* (leaf) (Aloe Vera Gel) Juice | This ingredient functions mostly as a skin conditioning agent. |
| *Helianthus Annuus* (Sunflower) Oil | This ingredient functions mostly as an occlusive. |
| Tapioca Starch | Tapioca Starch is the starch obtained from the roots of Manihot esculenta. It consists primarily of amylose and amylopectin. This is typically used as a viscosity increasing agent. |
| Saccharide Isomerate | Saccharide Isomerate is a carbohydrate complex formed from a base catalyzed rearrangement of a mixture of saccharides. Typically used as a skin conditioning agent or humectant. |
| Caramel color | Caramel is a concentrated sugary material obtained from heating sucrose or glucose solutions. Typically used as a colorant and/or fragrance ingredient. |
| Hydroxyethylcellulose | This is a modified cellulose polymer which contains hydroxyethyl side chains. Typically function as a binder, emulsion stabilizer, film former, or viscosity increasing agent. |

TABLE 4-continued

| Name | Illustrative Function* |
| --- | --- |
| Ascorbic Acid (Vitamin C) | This ingredient is a skin conditioning agent and antioxidant. |
| *Glycine Soja* (Soybean) Oil | *Glycine Soja* is a plant derived oil used in cosmetic products for its skin conditioning, occlusive, emollient, and moisturizing properties. |
| Xanthan Gum | Xanthan Gum is a polysaccharide derived from the fermentation of carbohydrates. Xanthan Gum is derived from glucose or corn syrup. In cosmetics and personal care products, Xanthan Gum may function as a binder, emulsion stabilizer, skin-conditioning agent - miscellaneous, surfactant - emulsifying agent, or viscosity increasing agent - aqueous. Xanthan Gum is a very large molecule with an average molecular weight of 1,000,000 or more. Xanthan Gum dissolves readily in water with stirring, resulting in highly viscous solutions at low concentrations. |
| Glycerin | Glycerin is reported to function in cosmetics as a denaturant, fragrance ingredient, hair conditioning agent, humectant, oral care agent, oral health care drug, skin protectant, skin-conditioning agent, and viscosity decreasing agent. Glycerin is a clear, syrupy liquid. It can be in a crystallized state. Glycerin is completely miscible with water, methanol, ethanol, and the isomers of propanol, butanol, and pentanol. Natural glycerin is obtained as a by-product in the conversion of fats and oils into fatty acids or fatty acid methyl esters. |
| Gluconolactone | This ingredient functions mostly as a humectant. |
| Sodium Benzoate | Sodium benzoate occurs naturally along with benzoic acid and its esters in many foods. Fruits and vegetables are rich sources. Other sources include seafood and dairy products. |
| *Camellia Sinensis* (Green Tea) (leaf) Extract | These ingredients function mostly as antioxidants and skin conditioning agents. The constituents of *C. sinensis* include amino acids, carotenoids, catechins, enzymes, flavonoids, and glycosides. The concentrations of these constituents in plants are influenced by growing conditions, geographical location, soil conditions, and processing. Generally recognized as safe (GRAS) for use in food products by the FDA. |
| Calcium Gluconate | This ingredient is the calcium salt of gluconic acid. Typically used as a chelating agent or skin conditioning agent. |
| bioGlitter | This ingredient provides a natural sparkle to the topical composition |
| Parfum (fragrance) | Natural fragrance. |
| *Lavandula Angustifolia* (Lavender) Oil | An unspecified preparation of the lavender plant. May be used as a Fragrance Ingredient; Skin-Conditioning Agent; or, Miscellaneous. |
| Hyaluronic Acid | This ingredient functions as a skin-conditioning agent and/or as a viscosity increasing agent in cosmetic formulations. Has been shown to increase the moisture level of damaged skin and to accelerate damage repair. |
| Jojoba Esters | This ingredient is typically used as an emollient or skin conditioning agent. |

At least one preferred embodiment includes a (certified) natural (after-sun, tan-enhancing) bronzer, skin toner, or moisturizer composition with natural sparkle or shimmer, preferably for use in toning or moisturizer skin and/or enhancing skin pigmentation or tan after exposure to ultraviolet radiation. In some embodiments, the composition can comprise one or more natural, organic, and/or plant-derived ingredients, such as *Aloe vera* (juice) extract, caprylic/capric triglyceride, cetearyl olivate, sorbitan olivate, cosmetic bioglitter, *Helianthus annuus* (sunflower) seed oil, propanediol, xanthan gum, natural perfume or fragrance, glycerin, tapioca starch, saccharide isomerate, caramel color, gluconolactone, hydroxyethyl cellulose, sodium benzoate, ascorbic acid, *Lavandula angustifolia* (lavender) oil, *Camellia sinensis* (green tea) (leaf) extract, tocopherol, jojoba esters, hyaluronic acid or sodium hyaluronate, and water. Each of the foregoing ingredients can be acceptable under the rigid standard of the prestigious Natural Products Association (in appropriate amount(s), for some ingredients). Some embodiments can include or comprise each of the foregoing ingredients. Some embodiments can consist or consist essentially of each of the foregoing ingredients. Alternative embodiments can include or comprise fewer than all of the foregoing ingredients. Some embodiments can include or comprise a combination of two or more of the foregoing ingredients.

In some embodiments, the composition (i) consists (essentially) of certified natural and/or organic ingredients or (ii) is (substantially) free or devoid of synthetic ingredients that negate natural certification. In some embodiments, the composition can include (trace amount(s) of) one or more non-natural or synthetic ingredients, while still maintaining certified status. For instance, various natural ingredient extraction processes use chemicals that remain (in trace amounts) in the final, extracted plant product. Other naturally occurring, plant-based compounds are processed or altered during extraction, formulation, or processing, thereby becoming (technically) a non-natural compound. Moreover, a small amount of one or more non-natural or synthetic ingredient(s) may be included in one or more embodiments (e.g., preservatives, solvents, conditioning agents, etc.). Certification (e.g., as "natural" or "organic") may not be negated by such ingredients being included in compositions of the present disclosure.

In some embodiments, the (certified) natural (after-sun, tan-enhancing) bronzer, skin toner, or moisturizer composition with natural sparkle or shimmer can include (about) 1-12%, w/w, *Aloe vera* (juice) extract, preferably about 6%, w/w, *Aloe vera* (juice) extract.

In some embodiments, the (certified) natural (after-sun, tan-enhancing) bronzer, skin toner, or moisturizer composition with natural sparkle or shimmer can include (about) 0.5-10%, w/w, caprylic/capric triglyceride, preferably about 3%, w/w, caprylic/capric triglyceride.

In some embodiments, the (certified) natural (after-sun, tan-enhancing) bronzer, skin toner, or moisturizer composition with natural sparkle or shimmer can include (about) 0.5-6%, w/w, cetearyl olivate, preferably about 2.5%, w/w, cetearyl olivate.

In some embodiments, the (certified) natural (after-sun, tan-enhancing) bronzer, skin toner, or moisturizer composition with natural sparkle or shimmer can include (about) 0.5-6%, w/w, sorbitan olivate, preferably about 2.5%, w/w, sorbitan olivate.

In some embodiments, the (certified) natural (after-sun, tan-enhancing) bronzer, skin toner, or moisturizer composition with natural sparkle or shimmer can include (about) 0.05-5%, w/w, cosmetic bioglitter, preferably about 1%, w/w, cosmetic bioglitter.

In some embodiments, the (certified) natural (after-sun, tan-enhancing) bronzer, skin toner, or moisturizer composition with natural sparkle or shimmer can include (about) 0.5-6%, w/w, *Helianthus annuus* (sunflower) seed oil, preferably about 2%, w/w, *Helianthus annuus* (sunflower) seed oil.

In some embodiments, the (certified) natural (after-sun, tan-enhancing) bronzer, skin toner, or moisturizer composition with natural sparkle or shimmer can include (about) 0.5-6%, w/w, propanediol, preferably about 2%, w/w, propanediol.

In some embodiments, the (certified) natural (after-sun, tan-enhancing) bronzer, skin toner, or moisturizer composition with natural sparkle or shimmer can include (about) 0.01-2%, w/w, xanthan gum, preferably about 0.1%, w/w, xanthan gum.

In some embodiments, the (certified) natural (after-sun, tan-enhancing) bronzer, skin toner, or moisturizer composition with natural sparkle or shimmer can include (about) 0.01-2%, w/w, natural perfume or fragrance, preferably about 0.35%, w/w, natural perfume or fragrance.

In some embodiments, the (certified) natural (after-sun, tan-enhancing) bronzer, skin toner, or moisturizer composition with natural sparkle or shimmer can include (about) 0.5-6%, w/w, glycerin, preferably about 2%, w/w, glycerin.

In some embodiments, the (certified) natural (after-sun, tan-enhancing) bronzer, skin toner, or moisturizer composition with natural sparkle or shimmer can include (about) 0.5-5%, w/w, tapioca starch, preferably about 1.5%, w/w, tapioca starch.

In some embodiments, the (certified) natural (after-sun, tan-enhancing) bronzer, skin toner, or moisturizer composition with natural sparkle or shimmer can include (about) 0.05-5%, w/w, saccharide isomerate, preferably about 1-1.5%, w/w, saccharide isomerate.

In some embodiments, the (certified) natural (after-sun, tan-enhancing) bronzer, skin toner, or moisturizer composition with natural sparkle or shimmer can include (about) 0.05-5%, w/w, caramel color, preferably about 1%, w/w, caramel color.

In some embodiments, the (certified) natural (after-sun, tan-enhancing) bronzer, skin toner, or moisturizer composition with natural sparkle or shimmer can include (about) 0.05-2.5%, w/w, gluconolactone, preferably about 0.6%, w/w, gluconolactone.

In some embodiments, the (certified) natural (after-sun, tan-enhancing) bronzer, skin toner, or moisturizer composition with natural sparkle or shimmer can include (about) 0.05-2.5%, w/w, hydroxyethyl cellulose, preferably about 0.4%, w/w, hydroxyethyl cellulose.

In some embodiments, the (certified) natural (after-sun, tan-enhancing) bronzer, skin toner, or moisturizer composition with natural sparkle or shimmer can include (about) 0.05-2.5%, w/w, sodium benzoate, preferably about 0.35%, w/w, sodium benzoate. In some embodiments, the composition can be (substantially) free or devoid of sodium benzoate.

In some embodiments, the (certified) natural (after-sun, tan-enhancing) bronzer, skin toner, or moisturizer composition with natural sparkle or shimmer can include (about) 0.05-2.5%, w/w, ascorbic acid, preferably about 0.25%, w/w, ascorbic acid.

In some embodiments, the (certified) natural (after-sun, tan-enhancing) bronzer, skin toner, or moisturizer composition with natural sparkle or shimmer can include (about) 0.05-2.5%, w/w, *Lavandula angustifolia* (lavender) oil, preferably about 0.25%, w/w, *Lavandula angustifolia* (lavender) oil.

In some embodiments, the (certified) natural (after-sun, tan-enhancing) bronzer, skin toner, or moisturizer composition with natural sparkle or shimmer can include (about) 0.01-2%, w/w, *Camellia sinensis* (green tea) (leaf) extract, preferably about 0.1-0.2%, w/w, *Camellia sinensis* (green tea) (leaf) extract.

In some embodiments, the (certified) natural (after-sun, tan-enhancing) bronzer, skin toner, or moisturizer composition with natural sparkle or shimmer can include (about) 0.01-2%, w/w, tocopherol, preferably about 0.2-0.25%, w/w, tocopherol.

In some embodiments, the (certified) natural (after-sun, tan-enhancing) bronzer, skin toner, or moisturizer composition with natural sparkle or shimmer can include (about) 0.01-2%, w/w, jojoba esters, preferably about 0.2%, w/w, jojoba esters.

In some embodiments, the (certified) natural (after-sun, tan-enhancing) bronzer, skin toner, or moisturizer composition with natural sparkle or shimmer can include (about) 0.01-2%, w/w, hyaluronic acid or sodium hyaluronate, preferably about 0.2%, w/w, hyaluronic acid or sodium hyaluronate.

In some embodiments, the (certified) natural (after-sun, tan-enhancing) bronzer, skin toner, or moisturizer composition with natural sparkle or shimmer can include water, preferably q.s. to 100%.

Figure 4:
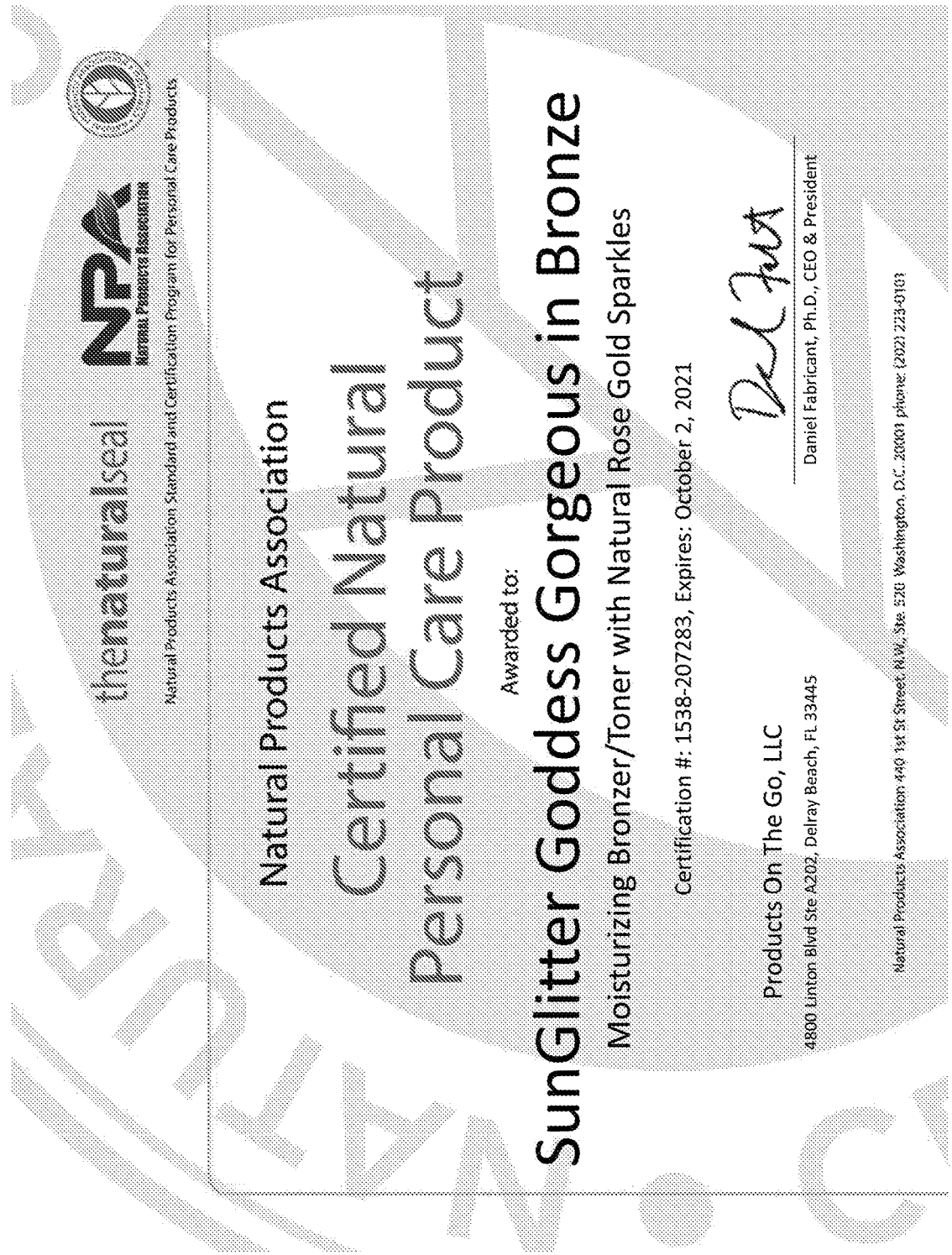
FIG. 4 is a copy of an actual, valid certification from the Natural Products Association of a Natural Moisturizing Bronzer/Toner with Natural Sparkles composition in accordance with one or more embodiments of the present disclosure.

Each of the natural (after-sun, tan-enhancing) bronzer, skin toner, or moisturizer composition with natural sparkle or shimmer, according to embodiments of the present disclosure have been certified and granted status as a "Certified Natural Personal Care Product" by the prestigious Natural Products Associate (NPA). See FIG. 4. The "Natural Seal" of the NPA sets the inventive compositions apart from other similar products in the art.

Some embodiments can include a method of toning or moisturizer skin and/or enhancing skin pigmentation or tan after exposure to ultraviolet radiation. The method can comprise applying a composition of the present disclosure to a selected skin area following exposure (of the selected skin area) to ultraviolet radiation. An illustrative method of toning or moisturizer skin and/or enhancing skin pigmentation or tan after exposure to ultraviolet radiation can include (1) applying a (certified) natural (after-sun, tan-enhancing) bronzer, skin toner, or moisturizer composition with natural sparkle or shimmer (in accordance with an embodiment of the present disclosure) to a selected skin area, and (2) leaving the composition in contact with the skin area for a first period of time (e.g., following a period of exposure to ultraviolet radiation).

In some embodiments the natural (after-sun, tan-enhancing) bronzer, skin toner, or moisturizer composition with natural sparkle or shimmer may be (at least partially) absorbed into the skin so that the base medium is no longer visible on the surface of the skin, but the natural sparkle or shimmer is still visible. In other embodiments the natural composition may remain visible on the surface of the skin after it is applied. The natural composition may be applied to skin surface areas which typically experience sun exposure. Areas where the skin typically experiences sun exposure include the face, forehead, neck, shoulders, arms, legs, feet, back, chest, stomach, and so forth.

CONCLUSIONS

*Cosmetic Use: The Cosmetic Ingredient Review (CIR) Expert Panel assesses the safety of cosmetic ingredients based on the expected use of these ingredients in cosmetics. The Panel reviews data received from the U.S. Food and Drug Administration (FDA) and the cosmetics industry to determine the expected cosmetic use. The FDA collects data from manufacturers on the use of individual ingredients in cosmetics, by cosmetic product category, through the FDA Voluntary Cosmetic Registration Program (VCRP). Data from the cosmetic industry are submitted in response to a survey of the maximum reported use concentrations, by category, conducted by the Personal Care Products Council.

The disclosed and/or described embodiments are to be considered in all respects only as illustrative and not restrictive. While various aspects, features and embodiments have been disclosed herein, other aspects, features and embodiments are contemplated but may not be disclosed. For instance, certain well-known aspects, features and embodiments are not described herein in particular detail in order to avoid obscuring aspects of the described embodiments. Such aspects, features and embodiments are, however, contemplated herein. Thus, while a number of methods and components similar or equivalent to those described herein can be used to practice embodiments of the present disclosure, only certain components and methods are described herein.

The present disclosure may also be embodied in other specific forms without departing from its spirit or essential characteristics. While certain embodiments and details have been included herein and in the attached disclosure for purposes of illustrating embodiments of the present disclosure, it will be apparent to those skilled in the art that various changes in the methods, products, devices, and apparatus disclosed herein may be made without departing from the scope of the disclosure or of the invention, which is defined in the appended claims. For instance, various alterations and/or modifications and additional applications of the inventive features illustrated herein, and additional applications of the principles illustrated herein, which would occur to one skilled in the relevant art and having possession of this disclosure, can be made to the illustrated embodiments without departing from the spirit and scope of the invention as defined by the claims, and are to be considered within the scope of this disclosure.

It will be appreciated that certain embodiments (e.g., compositions, formulations, method, etc.) may include, incorporate, or otherwise comprise features (e.g., properties, components, ingredients, elements, parts, portions, steps, etc.) described in other embodiments disclosed and/or described herein. Accordingly, the various features of certain embodiments can be compatible with, combined with, included in, and/or incorporated into other embodiments of the present disclosure. Thus, disclosure of certain features relative to a one embodiment of the present disclosure should not be construed as limiting application or inclusion of said features to the specific embodiment. Rather, it will be appreciated that other embodiments can also include said features without necessarily departing from the scope of the present disclosure. Moreover, unless a feature is described as requiring another feature in combination therewith, any feature herein may be combined with any other feature of a same or different embodiment disclosed herein.

The scope of the invention is, therefore, indicated by the appended claims rather than by the foregoing description. All changes which come within the meaning and range of equivalency of the claims are to be embraced within their scope.

What is claimed is:

1. A diaper rash composition, comprising:
about 12%, w/w, zinc oxide;
about 20%, w/w, *Aloe vera* juice or extract;
about 11.5%, w/w, beeswax;
about 11%, w/w, *Butyrospermum Parkii* butter;
about 3%, w/w, *Cocos nucifera* oil;
about 0.2%, w/w, *Lavandula angustifolia* oil;
about 0.1%, w/w, *Cucumis sativus* extract;
about 0.1%, w/w, *Glycyrrhiza glabra* extract;
about 0.1%, w/w, *Calendula officinalis* extract;
about 0.1%, w/w, tocopherol;
about 0.1%, w/w, *Chamomilla recutita* oil; and
*Helianthus annuus* seed oil q.s. to 100%.

2. A diaper rash composition, comprising:
5-20%, w/w, zinc oxide;
10-30%, w/w, *Aloe vera* extract;
5-15%, w/w, beeswax;
5-15%, w/w, *Butyrospermum Parkii* butter;
1-5%, w/w, *Cocos nucifera* oil;
0.01-1%, w/w, *Lavandula angustifolia* oil;
0.01-1%, w/w, *Cucumis sativus* extract;
0.01-1%, w/w, *Glycyrrhiza glabra* extract;
0.01-1%, w/w, *Calendula officinalis* extract;
0.01-1%, w/w, tocopherol;
0.01-1%, w/w, *Chamomilla recutita* oil; and
*Helianthus annuus* seed oil q.s. to 100%.

3. A diaper rash composition, comprising:
5-20%, w/w, zinc oxide;
10-30%, w/w, *Aloe vera* or extract;
5-15%, w/w, beeswax;
5-15%, w/w, *Butyrospermum Parkii* butter;
1-5%, w/w, *Cocos nucifera* oil;
0.01-1%, w/w, *Cucumis sativus* extract;
0.01-1%, w/w, *Calendula officinalis* extract;
0.01-1%, w/w, tocopherol; and
*Helianthus annuus* seed oil q.s. to 100%.

* * * * *